US009978960B2

(12) United States Patent
Inoue et al.

(10) Patent No.: US 9,978,960 B2
(45) Date of Patent: May 22, 2018

(54) ORGANOMETALLIC IRIDIUM COMPLEX, LIGHT-EMITTING ELEMENT, LIGHT-EMITTING DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Tomoya Yamaguchi, Kanagawa (JP); Hiromi Seo, Kanagawa (JP); Tatsuyoshi Takahashi, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 907 days.

(21) Appl. No.: 14/300,695

(22) Filed: Jun. 10, 2014

(65) Prior Publication Data
US 2014/0367662 A1 Dec. 18, 2014

(30) Foreign Application Priority Data

Jun. 14, 2013 (JP) ................................. 2013-125429

(51) Int. Cl.
*H01L 51/00* (2006.01)
*C07F 15/00* (2006.01)

(52) U.S. Cl.
CPC ...... *H01L 51/0085* (2013.01); *C07F 15/0033* (2013.01)

(58) Field of Classification Search
CPC .................. H01L 51/0085; H01L 51/5016
See application file for complete search history.

(56) References Cited

U.S. PATENT DOCUMENTS

| | | | |
|---|---|---|---|
| 6,303,238 B1 | 10/2001 | Thompson et al. |
| 6,565,994 B2 | 5/2003 | Igarashi |
| 6,734,457 B2 | 5/2004 | Yamazaki et al. |
| 6,780,528 B2 | 8/2004 | Tsuboyama et al. |
| 6,821,645 B2 | 11/2004 | Igarashi |
| 6,821,646 B2 | 11/2004 | Tsuboyama et al. |
| 6,835,469 B2 | 12/2004 | Kwong et al. |
| 6,902,830 B2 | 6/2005 | Thompson et al. |
| 6,911,271 B1 | 6/2005 | Lamansky et al. |
| 6,939,624 B2 | 9/2005 | Lamansky et al. |
| 6,949,878 B2 | 9/2005 | Suzuri et al. |
| 6,953,628 B2 | 10/2005 | Kamatani et al. |
| 7,001,536 B2 | 2/2006 | Thompson et al. |
| 7,094,477 B2 | 8/2006 | Kamatani et al. |
| 7,147,935 B2 | 12/2006 | Kamatani et al. |
| 7,175,922 B2 | 2/2007 | Jarikov et al. |
| 7,183,010 B2 | 2/2007 | Jarikov |
| 7,220,495 B2 | 5/2007 | Tsuboyama et al. |
| 7,238,437 B2 | 7/2007 | Igarashi et al. |
| 7,238,806 B2 | 7/2007 | Inoue et al. |
| 7,291,406 B2 | 11/2007 | Thompson et al. |
| 7,332,857 B2 | 2/2008 | Seo et al. |
| 7,339,317 B2 | 3/2008 | Yamazaki |
| 7,355,340 B2 | 4/2008 | Shitagaki et al. |
| 7,381,479 B2 | 6/2008 | Lamansky et al. |
| 7,400,087 B2 | 7/2008 | Yamazaki |
| 7,413,816 B2 | 8/2008 | Inoue et al. |
| 7,473,575 B2 | 1/2009 | Yamazaki et al. |
| 7,482,451 B2 | 1/2009 | Thompson et al. |
| 7,482,626 B2 | 1/2009 | Yamazaki et al. |
| 7,537,844 B2 | 5/2009 | Thompson et al. |
| 7,553,560 B2 | 6/2009 | Lamansky et al. |

(Continued)

FOREIGN PATENT DOCUMENTS

CN 001957645 A 5/2007
CN 101111506 A 1/2008
(Continued)

OTHER PUBLICATIONS

Chinese Office Action re Application No. CN 201480033694.7, dated Apr. 20, 2017.
International Search Report re Application No. PCT/JP2014/064357, dated Jul. 15, 2014.
Written Opinion re Application No. PCT/JP2014/064357, dated Jul. 15, 2014.
Yamamoto, T. et al., "Preparation of New Electron-Accepting π-Conjugated Polyquinoxalines. Chemical and Electrochemical Reduction, Electrically Conducting Properties, and Use in Light-Emitting Diodes," Journal of The American Chemical Society, 1996, vol. 118, No. 16, pp. 3930-3937.
Tsutsui, T. et al., "Electroluminescence in Organic Thin Films," Photochemical Processes in Organized Molecular Systems, 1991, pp. 437-450.

(Continued)

*Primary Examiner* — Alexander R Pagano
*Assistant Examiner* — Ebenezer O Sackey
(74) *Attorney, Agent, or Firm* — Husch Blackwell LLP

(57) ABSTRACT

An organometallic iridium complex that has high emission efficiency and a long lifetime and emits deep red light (emission wavelength: around 700 nm) is provided. The organometallic iridium complex has a ligand that is represented by General Formula (G0) and has at least a dimethyl phenyl group and a quinoxaline skeleton.

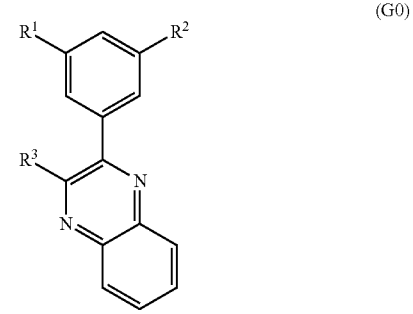

(G0)

In the formula, $R^1$ to $R^3$ separately represent an alkyl group having 1 to 6 carbon atoms, a phenyl group, or a phenyl group having an alkyl group having 1 to 6 carbon atoms as a substituent.

8 Claims, 19 Drawing Sheets

(56) References Cited

U.S. PATENT DOCUMENTS

| | | |
|---|---|---|
| 7,597,967 B2 | 10/2009 | Kondakova et al. |
| 7,652,283 B2 | 1/2010 | Inoue et al. |
| 7,737,437 B2 | 6/2010 | Yamazaki et al. |
| 7,771,844 B2 | 8/2010 | Inoue et al. |
| 7,795,429 B2 | 9/2010 | Inoue et al. |
| 7,807,839 B2 | 10/2010 | Inoue et al. |
| 7,811,677 B2 | 10/2010 | Ohsawa et al. |
| 7,883,787 B2 | 2/2011 | Thompson et al. |
| 7,901,792 B2 | 3/2011 | Egawa et al. |
| 7,915,409 B2 | 3/2011 | Inoue et al. |
| 7,939,821 B2 | 5/2011 | Inoue et al. |
| 7,951,471 B2 | 5/2011 | Inoue et al. |
| 7,993,760 B2 | 8/2011 | Komori et al. |
| 8,034,465 B2 | 10/2011 | Liao et al. |
| 8,173,277 B2 | 5/2012 | Egawa et al. |
| 8,227,600 B2 | 7/2012 | Inoue et al. |
| 8,274,214 B2 | 9/2012 | Ikeda et al. |
| 8,278,444 B2 | 10/2012 | Inoue et al. |
| 8,283,052 B2 | 10/2012 | Egawa et al. |
| 8,399,665 B2 | 3/2013 | Inoue et al. |
| 8,512,880 B2 | 8/2013 | Inoue et al. |
| 8,569,486 B2 | 10/2013 | Inoue et al. |
| 8,574,726 B2 | 11/2013 | Thompson et al. |
| 8,623,523 B2 | 1/2014 | Egawa et al. |
| 8,637,167 B2 | 1/2014 | Ohsawa et al. |
| 8,853,680 B2 | 10/2014 | Yamazaki et al. |
| 8,889,266 B2 | 11/2014 | Inoue et al. |
| 8,963,127 B2 | 2/2015 | Pieh et al. |
| 8,981,355 B2 | 3/2015 | Seo |
| 8,993,129 B2 | 3/2015 | Endo et al. |
| 8,994,263 B2 | 3/2015 | Shitagaki et al. |
| 9,034,483 B2 | 5/2015 | Alleyne et al. |
| 9,054,317 B2 | 6/2015 | Monkman et al. |
| 9,130,184 B2 | 9/2015 | Seo et al. |
| 9,159,942 B2 | 10/2015 | Seo et al. |
| 9,175,213 B2 | 11/2015 | Seo et al. |
| 9,356,250 B2 | 5/2016 | Ohsawa et al. |
| 9,604,928 B2 | 3/2017 | Shitagaki et al. |
| 2002/0034659 A1 | 3/2002 | Nishi et al. |
| 2002/0068190 A1 | 6/2002 | Tsuboyama et al. |
| 2003/0072964 A1 | 4/2003 | Kwong et al. |
| 2003/0175553 A1 | 9/2003 | Thompson et al. |
| 2003/0197183 A1 | 10/2003 | Grushin et al. |
| 2003/0218418 A9 | 11/2003 | Sato et al. |
| 2004/0102632 A1 | 5/2004 | Thompson et al. |
| 2004/0230061 A1 | 11/2004 | Seo et al. |
| 2005/0003232 A1 | 1/2005 | Shitagaki et al. |
| 2005/0048310 A1 | 3/2005 | Cocchi et al. |
| 2005/0065342 A1 | 3/2005 | Shitagaki et al. |
| 2005/0191527 A1 | 9/2005 | Fujii et al. |
| 2005/0221116 A1 | 10/2005 | Cocchi et al. |
| 2006/0078758 A1 | 4/2006 | Lin |
| 2006/0134464 A1 | 6/2006 | Nariyuki |
| 2006/0240278 A1 | 10/2006 | Hatwar et al. |
| 2007/0037010 A1 | 2/2007 | Vestweber et al. |
| 2007/0090756 A1 | 4/2007 | Okada et al. |
| 2007/0213527 A1 | 9/2007 | Inoue et al. |
| 2007/0241667 A1 | 10/2007 | Ohsawa et al. |
| 2008/0076922 A1 | 3/2008 | Inoue et al. |
| 2008/0113216 A1 | 5/2008 | Inoue et al. |
| 2009/0033209 A1 | 2/2009 | Seo et al. |
| 2009/0085476 A1 | 4/2009 | Park et al. |
| 2010/0044689 A1 | 2/2010 | Nishimura et al. |
| 2010/0237342 A1 | 9/2010 | Yamazaki et al. |
| 2011/0001133 A1 | 1/2011 | Inoue et al. |
| 2011/0024732 A1 | 2/2011 | Ohsawa et al. |
| 2011/0057560 A1 | 3/2011 | Inoue et al. |
| 2011/0082296 A1 | 4/2011 | Inoue et al. |
| 2011/0196152 A1 | 8/2011 | Inoue et al. |
| 2012/0126692 A1 | 5/2012 | Ise et al. |
| 2012/0217487 A1 | 8/2012 | Yamazaki |
| 2014/0081021 A1 | 3/2014 | Inoue et al. |
| 2014/0121372 A1 | 5/2014 | Inoue et al. |
| 2015/0069352 A1 | 3/2015 | Kim et al. |
| 2015/0255734 A1 | 9/2015 | Alleyne et al. |

FOREIGN PATENT DOCUMENTS

| | | |
|---|---|---|
| CN | 101575352 A | 11/2009 |
| CN | 102757782 A | 10/2012 |
| CN | 102924526 A | 2/2013 |
| EP | 1 202 608 A2 | 5/2002 |
| EP | 2 999 021 A1 | 3/2016 |
| JP | 63-159856 A | 7/1988 |
| JP | 06-207169 A | 7/1994 |
| JP | 11-329729 A | 11/1999 |
| JP | 2000-231988 A | 8/2000 |
| JP | 2003-040873 A | 2/2003 |
| JP | 2004-155728 A | 6/2004 |
| JP | 2005-239648 A | 9/2005 |
| JP | 2005-298483 A | 10/2005 |
| JP | 2006-073992 A | 3/2006 |
| JP | 2006-151887 A | 6/2006 |
| JP | 2006-182772 A | 7/2006 |
| JP | 2007-137872 | 6/2007 |
| JP | 2007-314541 A | 12/2007 |
| JP | 2008-069221 | 3/2008 |
| JP | 2008-235874 A | 10/2008 |
| JP | 2008-288344 A | 11/2008 |
| JP | 2009-293037 A | 12/2009 |
| JP | 2009-298794 A | 12/2009 |
| JP | 2011-049512 A | 3/2011 |
| JP | 2011-098958 A | 5/2011 |
| JP | 2012-503043 | 2/2012 |
| JP | 2012-097102 A | 5/2012 |
| JP | 2014-058457 A | 4/2014 |
| KR | 2007-0015605 A | 2/2007 |
| KR | 2007-0086916 A | 8/2007 |
| KR | 10-1187399 B1 | 10/2012 |
| WO | 2005115061 A1 * | 12/2005 |
| WO | WO 2005/115061 A1 | 12/2005 |
| WO | WO 2006/059802 A1 | 6/2006 |
| WO | WO 2006/098460 A1 | 9/2006 |
| WO | WO 2008-035664 A1 | 3/2008 |
| WO | WO 2010/033550 A1 | 3/2010 |
| WO | WO 2011/013843 A1 | 2/2011 |

OTHER PUBLICATIONS

Baldo, M.A. et al., "Highly Efficient Phosphorescent Emission From Organic Electroluminescent Devices," Nature, Sep. 10, 1998, vol. 395, pp. 151-154.

Baldo, M.A. et al., "Very High-Efficiency Green Organic Light-Emitting Devices Based on Electrophosphorescence," Applied Physics Letters, Jul. 5, 1999, vol. 75, No. 1, pp. 4-6.

Tsutsui, T. et al., "High Quantum Efficiency in Organic Light-Emitting Devices With Iridium-Complex as a Triplet Emissive Center," Japanese Journal of Applied Physics, Dec. 15, 1999, vol. 38, No. 12B, pp. L1502-L1504.

O'Brien, D.F. et al., "Improved Energy Transfer in Electrophosphorescent Devices," Applied Physics Letters, Jan. 18, 1999, vol. 74, No. 3, pp. 442-444.

Baldo, M.A. et al., "High-Efficiency Fluorescent Organic Light-Emitting Devices Using a Phosphorescent Sensitizer," Nature, Feb. 17, 2000, vol. 403, pp. 750-753.

Tsutsui, T. "Mechanism of Organic El Element and Luminous Efficiency," Textbook of the Tsutsui, 3rd Seminar At Division of Organic Molecular Electronics and Bioelectronics, 1993, pp. 31-37, Division of Molecular Electronics and Bioelectronics The Japan Society of Applied Physics.

Tang, C.W, et al., "Organic Electroluminescent Diodes," Applied Physics Letters, Sep. 21, 1987, vol. 51, No. 12, pp. 913-915.

Thompson, M.E. et al., "Phosphorescent Materials and Devices," Proceedings of The 10th International Workshop on Inorganic and Organic Electroluminescence (EL'00), Dec. 4, 2000, pp. 35-38.

Duan, J.-P. et al., "New Iridium Complexes As Highly Efficient Orange-Red Emitters in Organic Light-Emitting Diodes," Advanced Materials, Feb. 5, 2003, vol. 15, No. 3, pp. 224-228.

Steel, P.J. et al., "Cyclometallated Compounds V. Double Cyclopalladation of Diphenyl Pyrazines and Related Ligands," Journal of Organometallic Chemistry, Oct. 2, 1990, vol. 395, No. 3, pp. 359-373.

(56) References Cited

OTHER PUBLICATIONS

Rasmussen, S.C. et al., "Synthesis and Characterization of a Series of Novel Rhodium and Iridium Complexes Containing Polypyridyl Bridging Ligands: Potential Uses in the Development of Multimetal Catalysts for Carbon Dioxide Reduction," Inorganic Chemistry, 1990, vol. 29, No. 20, pp. 3926-3932.
Zhang, G.L. et al., "Synthesis and Photoluminescence of a New Red Phosphorescent Iridium(III) Quinoxaline Complex," Chinese Chemical Letters, 2004, vol. 15, No. 11, pp. 1349-1352.
Seo, S. et al., "P-132: Long-Lived Deeply Red Phosphorescent Oleds Based on Electrochemically Stable IR Complexes," SID Digest '05: SID International Symposium Digest of Technical Papers, 2005, vol. 36, pp. 806-809.
Jakubke, H. et al., *Concise Encyclopedia Chemistry*, 1993, p. 490, Walter de Gruyter.
Ito, Y. et al., "Asymmetric Synthesis of Helical Poly(Quinoxaline-2, 3-Diyl)S by Palladium-Mediated Polymerization of 1, 2-Diisocyanobenzenes:Effective Control of the Screw-Sense by a Binaphthyl Group At the Chain-End," Journal of the American Chemical Society, 1998, vol. 120, No. 46, pp. 11880-11893.
Ito, Y. et al., "Living Polymerization of 1, 2-Diisocyanoarenes Promoted by (Quinoxalinyl)Nickel Complexes," Polymer Journal, 1992, vol. 24, No. 3, pp. 297-299.
Brooks, J. et al., "Synthesis and Characterization of Phosphorescent Cyclometalated Platinum Complexes," Inorganic Chemistry, 2002, vol. 41, No. 12, pp. 3055-3066.
Patani, G.A. et al., "Bioisosterism: A Rational Approach in Drug Design," Chemical Reviews, 1996, vol. 96, No. 8, pp. 3147-3176, American Chemical Society.
Williams, R.L. et al., "Synthesis, Characterization, and DNA Binding Properties of a Series of Ru, Pt Mixed-Metal Complexes," Inorganic Chemistry, 2003, vol. 42, No. 14, pp. 4394-4400.
Pine, S.H., *Organic Chemistry*, 1987, McGraw-Hill publishers, pp. 266-267.
Pine, S.H., *Organic Chemistry*, 1987, McGraw-Hill publishers, pp. 703-704.
Nishi, T. et al., "High Efficiency TFT-OLED Display With Iridium-Complex As Triplet Emissive Center," Proceedings of the 10th International Workshop on Inorganic and Organic Electroluminescence (EL'00), Dec. 4, 2000, pp. 353-356.
Fujii, H. et al., "04-0 Efficient Red Organometallic Phosphors Bearing 2,3-Diphenylquinoxalines and Their Application to Electrophosphorescent Diodes," Korea-Japan Joint Forum, Organic Materials For Electronics and Photonics, Nov. 3, 2004.
Kulikova, M.V. et al., "Effects of the Nature of the Ligand Environment and Metal Center on the Optical and Electrochemical Properties of Platinum (II) and Palladium (II) Ethylenediamine Complexes with Heterocyclic Cyclometalated Ligands," Russian Journal of General Chemistry, 2000, vol. 70, No. 2, pp. 163-170.
Balashev, K.P. et al., "Synthesis and Properties of Palladium(II) and Platinum(II)(2,3-diphenylquinoxalinato-C,N)ethylenediamine Complexes," Russian Journal of General Chemistry, Aug. 1, 1999, vol. 69, No. 8, pp. 1348-1349.
Fujii, H. et al., "Highly Efficient and Vivid-Red Phosphors Bearing 2,3-Diphenylquinoxaline Units and Their Application to Organic Light-Emitting Devices," IEICE Transactions on Electronics, Dec. 1, 2004, vol. E87-C, No. 12, pp. 2119-2121.

Yersin, H. et al., *Highly Efficient OLEDs with Phosphorescent Materials*, 2008, pp. 1-97,283-309, Wiley-VCH Verlag GmbH & Co.
Tokito,S. et al., "Improvement in Performance by Doping," Organic EL Display, Aug. 20, 2004, pp. 67-99, Ohmsha.
Jeon, W.S. et al., "Ideal Host and Guest System in Phosphorescent OLEDs," Organic Electronics, 2009, vol. 10, pp. 240-246, Elsevier.
Su, S-J et al., "RGB Phosphorescent Organic Light-Emitting Diodes by Using Host Materials with Heterocyclic Cores:Effect of Nitrogen Atom Orientations," Chemistry of Materials, 2011, vol. 23, No. 2, pp. 274-284.
Rausch, A.F. et al., "Matrix Effects on the Triplet State of the OLED Emitter Ir(4,6-dFppy)2(pic)(Firpic):Investigations by High-Resolution Optical Spectroscopy," Inorganic Chemistry, 2009, vol. 48, No. 5, pp. 1928-1937.
Gong, X. et al., "Phosphorescence from Iridium Complexes Doped into Polymer Blends," Journal of Applied Physics, Feb. 1, 2004, vol. 95, No. 3, pp. 948-953.
Zhao, Q. et al., "Synthesis and Photophysical, Electrochemical, and Electrophosphorescent Properties of a Series of Indium(111) Complexes Based on Quinoline Derivatives and Different β-Diketonate Ligands," Organometallics, Jun. 14, 2006, vol. 25, No. 15, pp. 3631-3638.
Hino, Y. et al., "Red Phosphorescent Organic Light-Emitting Diodes Using Mixture System of Small-Molecule and Polymer Host," Japanese Journal of Applied Physics, Apr. 21, 2005, vol. 44, No. 4B, pp. 2790-2794.
Tsuboyama, A. et al., "Homoleptic Cyclometalated Iridium Complexes with Highly Efficient Red Phosphorescence and Application to Organic Light-Emitting Diode," Journal of the American Chemical Society, 2003, vol. 125, No. 42, pp. 12971-12979.
Kondakova, M.E. et al., "High-Efficiency, Low-Voltage Phosphorescent Organic Light-Emitting Diode Devices with Mixed Host," Journal of Applied Physics, Nov. 4, 2008, vol. 104, pp. 094501-1-094501-17.
Chen, F-C. et al., "Triplet Exciton Confinement in Phosphorescent Polymer Light-Emitting Diodes," Applied Physics Letters, Feb. 17, 2003, vol. 82, No. 7, pp. 1006-1008.
Lee, J.Y. et al., "Stabilizing the Efficiency of Phosphorescent Organic Light-Emitting Diodes," SPIE Newsroom, Apr. 21, 2008, pp. 1-3.
Tokito, S. et al., "Confinement of Triplet Energy on Phosphorescent Molecules for Highly-Efficient Organic Blue-Light-Emitting Devices," Applied Physics Letters, Jul. 21, 2003, vol. 83, No. 3, pp. 569-571.
Endo, A. et al., "Efficient Up-Conversion of Triplet Excitons Into a Singlet State and Its Application for Organic Light Emitting Diodes," Applied Physics Letters, Feb. 24, 2011, vol. 98, No. 8, pp. 083302-1-083302-3.
Itano, K. et al., "Exciplex Formation at the Organic Solid-State Interface: Yellow Emission in Organic Light-Emitting Diodes Using Green-Fluorescent tris(8-quinolinolato)aluminum and Hole-Transporting Molecular Materials with Low Ionization Potentials," Applied Physics Letters, Feb. 9, 1998, vol. 72, No. 6, pp. 636-638.
Park, Y-S. et al., "Efficient Triplet Harvesting by Fluorescent Molecules Through Exciplexes for High Efficiency Organic Light-Emitting Diodes," Applied Physics Letters, Apr. 18, 2013, vol. 102, No. 15, pp. 153306-1-153306-5.

* cited by examiner

ORGANOMETALLIC IRIDIUM COMPLEX, LIGHT-EMITTING ELEMENT, LIGHT-EMITTING DEVICE, AND LIGHTING DEVICE

TECHNICAL FIELD

One embodiment of the present invention relates to an organometallic iridium complex, particularly, to an organometallic iridium complex that is capable of converting a triplet excited state into luminescence. In addition, one embodiment of the present invention relates to a light-emitting element, a light-emitting device, and a lighting device that include the organometallic iridium complex.

BACKGROUND ART

Organic compounds are brought into an excited state by absorbing light. Through this excited state, various reactions (photochemical reactions) are caused in some cases, or luminescence is generated in some cases. Therefore, the organic compounds have a wide range of applications.

As one example of the photochemical reactions, a reaction of singlet oxygen with an unsaturated organic molecule (oxygen addition) is known. Since the ground state of an oxygen molecule is a triplet state, oxygen in a singlet state (singlet oxygen) is not generated by direct photoexcitation. However, in the presence of another triplet excited molecule, singlet oxygen is generated to cause an oxygen addition reaction. In this case, a compound capable of forming the triplet excited molecule is referred to as a photosensitizer.

As described above, for generation of singlet oxygen, a photosensitizer capable of forming a triplet excited molecule by photoexcitation is needed. However, the ground state of an ordinary organic compound is a singlet state; therefore, photoexcitation to a triplet excited state is forbidden transition and generation of a triplet excited molecule is difficult. A compound that can easily cause intersystem crossing from the singlet excited state to the triplet excited state (or a compound that allows the forbidden transition of photoexcitation directly to the triplet excited state) is thus required as such a photosensitizer. In other words, such a compound can be used as the photosensitizer and is useful.

Such a compound often exhibits phosphorescence. Phosphorescence refers to luminescence generated by transition between different energies in multiplicity. In an ordinary organic compound, phosphorescence refers to luminescence generated in returning from the triplet excited state to the singlet ground state (in contrast, fluorescence refers to luminescence in returning from the singlet excited state to the singlet ground state). Application fields of a compound capable of exhibiting phosphorescence, that is, a compound capable of converting the triplet excited state into luminescence (hereinafter, referred to as a phosphorescent compound), include a light-emitting element including an organic compound as a light-emitting substance.

This light-emitting element has a simple structure in which a light-emitting layer including an organic compound that is a light-emitting substance is provided between electrodes. This light-emitting element attracts attention as a next-generation flat panel display element in terms of characteristics such as being thin and light in weight, high speed response, and direct current low voltage driving. A display device including this light-emitting element is superior in contrast, image quality, and has wide viewing angle.

The emission mechanism of a light-emitting element in which an organic compound is used as a light-emitting substance is a carrier injection type. That is, by applying voltage with a light-emitting layer interposed between electrodes, electrons and holes injected from the electrodes recombine to make the light-emitting substance excited, and light is emitted when the excited state returns to a ground state. As in the case of photoexcitation described above, types of the excited state include a singlet excited state ($S^*$) and a triplet excited state ($T^*$). The statistical generation ratio thereof in the light-emitting element is $S^*:T^*=1:3$.

In a compound which converts a singlet excited state into light emission (hereinafter referred to as a fluorescent compound), light emission from a triplet excited state (phosphorescence) is not observed at a room temperature but only light emission from a singlet excited state (fluorescence) is observed. Therefore, the internal quantum efficiency (the ratio of the number of generated photons to the number of injected carriers) of a light-emitting element including the fluorescent compound is assumed to have a theoretical limit of 25%, on the basis of $S^*:T^*=1:3$.

In contrast, in the case of a light-emitting element including the phosphorescent compound described above, the internal quantum efficiency thereof can be improved to 75% to 100% in theory; namely, the emission efficiency thereof can be 3 to 4 times as much as that of the light-emitting element including a fluorescent compound. For this reason, light-emitting elements using a phosphorescent compound have been recently under active development so that light-emitting elements with high efficiency can be achieved. As the phosphorescent compound, an organometallic complex that contains iridium or the like as a central metal has particularly attracted attention because of its high phosphorescence quantum yield (see, for example, Patent Document 1, Patent Document 2, and Patent Document 3).

REFERENCE

Patent Document

Patent Document 1: Japanese Published Patent Application No. 2007-137872
Patent Document 2: Japanese Published Patent Application No. 2008-069221
Patent Document 3: PCT International Publication No. 2008/035664

DISCLOSURE OF INVENTION

Phosphorescent materials emitting light of various colors have been developed as reported in Patent Documents 1 to 3, development of novel materials emitting light of colors for intended purposes is anticipated.

In view of the above, one embodiment of the present invention provides, as a novel substance, an organometallic iridium complex that has high emission efficiency and a long lifetime and emits near-infrared light (emission wavelength: around 700 nm). Another embodiment of the present invention provides an organometallic iridium complex that has high quantum efficiency. Another embodiment of the present invention provides a light-emitting element, a light-emitting device, or a lighting device that has high emission efficiency.

One embodiment of the present invention is an organometallic iridium complex having a ligand that is represented by General Formula (G0) and has at least a dimethyl phenyl group and a quinoxaline skeleton. Thus, one embodiment of the present invention is an organometallic iridium complex that has a structure represented by General Formula (G0).

(G0)

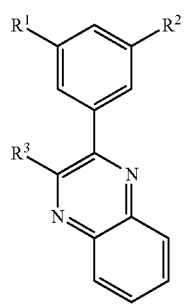

In the formula, $R^1$ to $R^3$ separately represent an alkyl group having 1 to 6 carbon atoms, a phenyl group, or a phenyl group having an alkyl group having 1 to 6 carbon atoms as a substituent.

Another embodiment of the present invention is an organometallic iridium complex represented by General Formula (G1).

(G1)

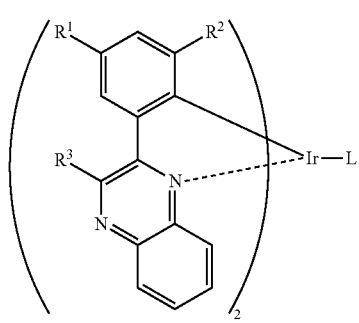

In the formula, $R^1$ to $R^3$ separately represent an alkyl group having 1 to 6 carbon atoms, a phenyl group, or a phenyl group having an alkyl group having 1 to 6 carbon atoms as a substituent. In addition, L represents a monoanionic ligand.

In the general formula (G1), the monoanionic ligand is preferably any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. A monoanionic bidentate chelate ligand having a beta-diketone structure is particularly preferable.

The monoanionic ligand is preferably a ligand represented by any of General Formulae (L1) to (L7).

(L1)

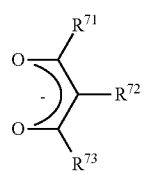

(L2)

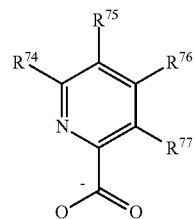

(L3)

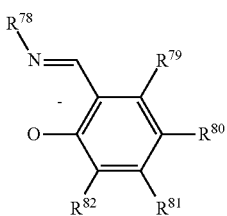

(L4)

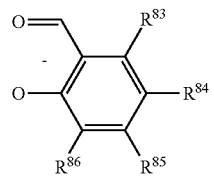

(L5)

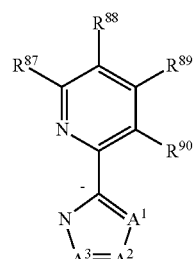

(L6)

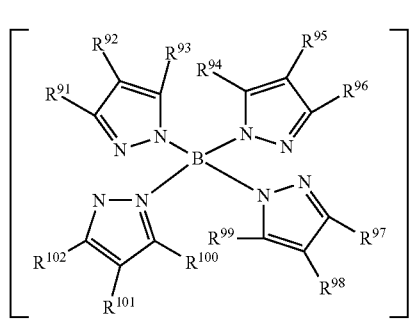

(L7)

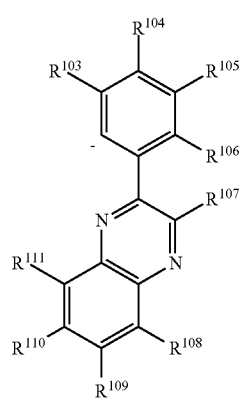

In the formulae, $R^{71}$ to $R^{111}$ separately represent hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms. In addition, $A^1$ to $A^3$ separately represent nitrogen, $sp^2$ hybridized carbon bonded to hydrogen, and $sp^2$ hybridized carbon having a substituent. The substituent represents an alkyl group having 1 to 6 carbon atoms, a halogen group, a haloalkyl group having 1 to 6 carbon atoms, and a phenyl group.

Another embodiment of the present invention is an organometallic iridium complex represented by General Formula (G2).

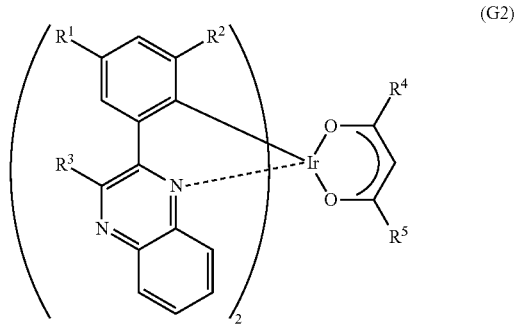

(G2)

In the formula, $R^1$ to $R^3$ separately represent an alkyl group having 1 to 6 carbon atoms, a phenyl group, or a phenyl group having an alkyl group having 1 to 6 carbon atoms as a substituent. In addition, $R^4$ and $R^5$ separately represent hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms.

Another embodiment of the present invention is an organometallic iridium complex represented by Structural Formula (100).

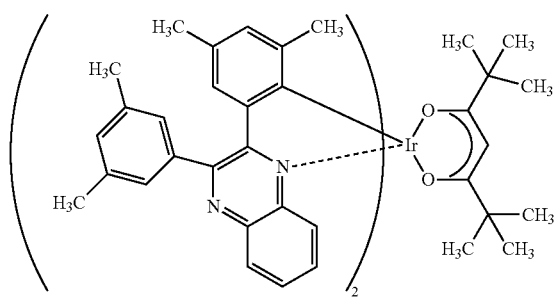

(100)

Another embodiment of the present invention is an organometallic iridium complex represented by Structural Formula (114).

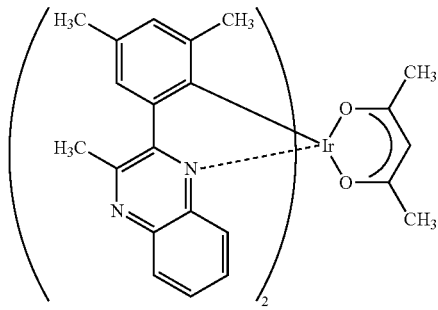

(114)

The organometallic iridium complex of one embodiment of the present invention is very effective for increasing efficiency of a light-emitting element because the organometallic iridium complex can emit phosphorescence, that is, emission resulting from energy transfer from a triplet excited state is possible. Thus, another embodiment of the present invention is a light-emitting element that includes the organometallic iridium complex of one embodiment of the present invention.

In addition, the present invention includes, in its scope, not only a light-emitting device including the light-emitting element but also a lighting device including the light-emitting device. The light-emitting device in this specification refers to an image display device and a light source (e.g., a lighting device). In addition, the light-emitting device includes, in its category, all of a module in which a light-emitting device is connected to a connector such as a flexible printed circuit (FPC), a tape carrier package (TCP), a module in which a printed wiring board is provided on the tip of a TCP, and a module in which an integrated circuit (IC) is directly mounted on a light-emitting element by a chip on glass (COG) method.

According to one embodiment of the present invention, an organometallic iridium complex that has high emission efficiency and a long lifetime and emits near-infrared light (emission wavelength: around 700 nm) can be provided as a novel substance. An organometallic iridium complex that has high quantum efficiency can also be provided. Note that the use of the novel organometallic iridium complex enables a light-emitting element, a light-emitting device, or a lighting device that has high emission efficiency to be provided. In addition, a light-emitting element, a light-emitting device, or a lighting device that consumes less power can be provided.

BEST MODE FOR CARRYING OUT THE INVENTION

Figure 1:
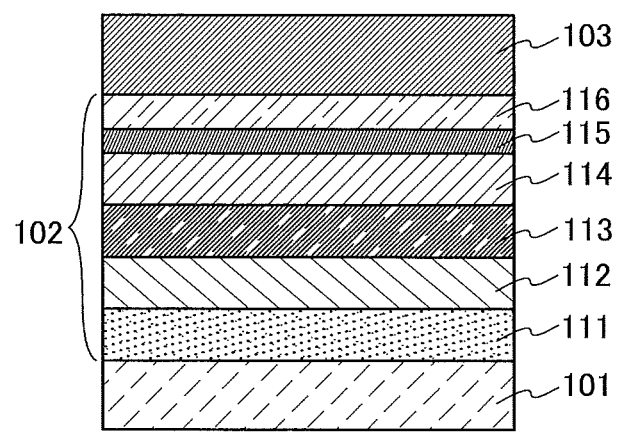
FIG. 1 illustrates a structure of a light-emitting element.

Hereinafter, embodiments of the present invention will be described with reference to the accompanying drawings. Note that the present invention is not limited to the following description, and various changes and modifications can be made without departing from the spirit and scope of the present invention. Therefore, the present invention should not be construed as being limited to the description in the following embodiments.

Embodiment 1

In this embodiment, an organometallic iridium complex of one embodiment of the present invention is described.

The organometallic iridium complex of one embodiment of the present invention is an organometallic iridium complex having a ligand that has at least a dimethyl phenyl group and a quinoxaline skeleton. Note that one embodiment of the organometallic iridium complex having the ligand that has at least the dimethyl phenyl group and the quinoxaline skeleton, which is described in this embodiment, is an organometallic iridium complex having a structure represented by General Formula (G1).

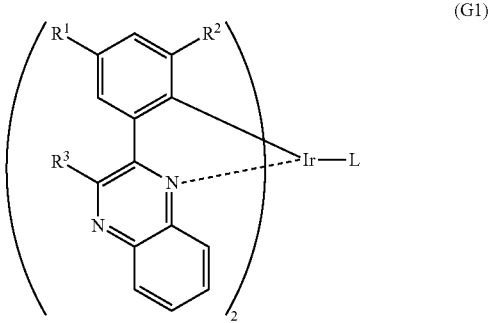

(G1)

In General Formula (G1), $R^1$ to $R^3$ separately represent an alkyl group having 1 to 6 carbon atoms, a phenyl group, or a phenyl group having an alkyl group having 1 to 6 carbon atoms as a substituent. In addition, L represents a monoanionic ligand.

In the general formula (G1), the monoanionic ligand is preferably any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. A monoanionic bidentate chelate ligand having a beta-diketone structure is particularly preferable.

The monoanionic ligand is preferably a ligand represented by any of General Formulae (L1) to (L7).

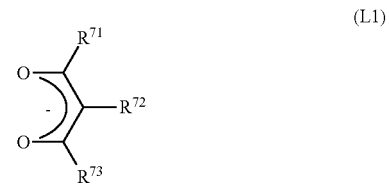

(L1)

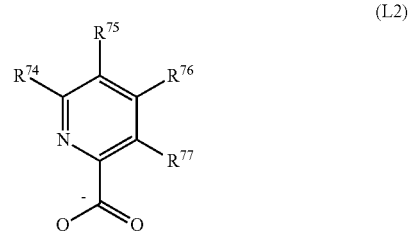

(L2)

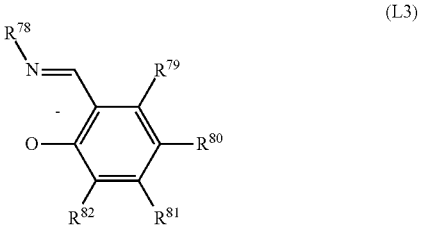

(L3)

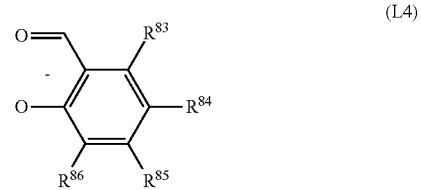

(L4)

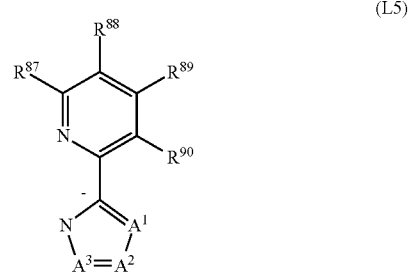

(L5)

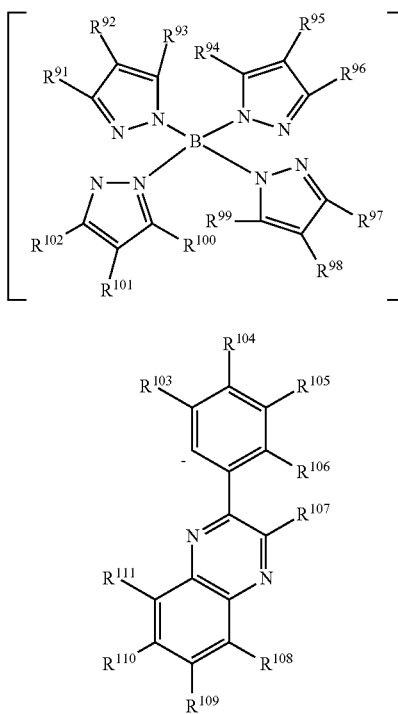
(L6)

(L7)

In the formulae, $R^{71}$ to $R^{111}$ separately represent hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms. In addition, $A^1$ to $A^3$ separately represent nitrogen, sp$^2$ hybridized carbon bonded to hydrogen, and sp$^2$ hybridized carbon having a substituent. The substituent represents an alkyl group having 1 to 6 carbon atoms, a halogen group, a haloalkyl group having 1 to 6 carbon atoms, and a phenyl group.

Note that specific examples of the substituted or unsubstituted alkyl group having 1 to 6 carbon atoms in $R^1$ to $R^3$ include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

Note that the organometallic iridium complex of one embodiment of the present invention has a structure in which a phenyl group that is bonded to a quinoxaline skeleton and bonded to iridium has two substituents that are any of an alkyl group having 1 to 6 carbon atoms, a phenyl group, and a phenyl group having an alkyl group having 1 to 6 carbon atoms as a substituent, and the two substituents are bonded to the 4-position and the 6-position of a 2-(2-quinoxalinyl)phenyl group bonded to iridium. This structure enables the emission wavelength (peak wavelength) of the organometallic iridium complex of one embodiment of the present invention to be longer than the emission wavelength of an organometallic iridium complex that does not have such substituents. In other words, the organometallic iridium complex of one embodiment of the present invention is a novel substance that emits near-infrared light and has high quantum efficiency.

Another embodiment of the present invention is an organometallic iridium complex represented by General Formula (G2).

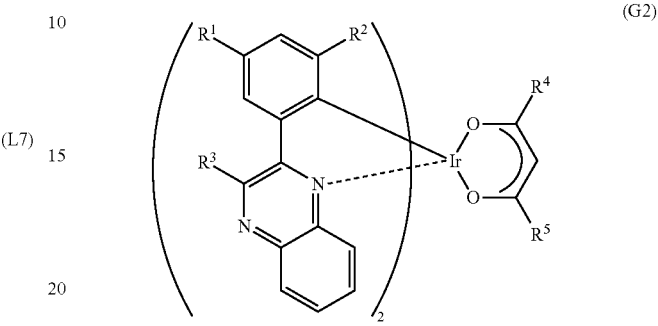
(G2)

In General Formula (G2), $R^1$ to $R^3$ separately represent an alkyl group having 1 to 6 carbon atoms, a phenyl group, or a phenyl group having an alkyl group having 1 to 6 carbon atoms as a substituent. In addition, $R^4$ and $R^5$ separately represent hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms.

Next, specific structural formulae of the above-described organometallic iridium complexes of embodiments of the present invention are shown (Structural Formulae (100) to (120)). Note that the present invention is not limited thereto.

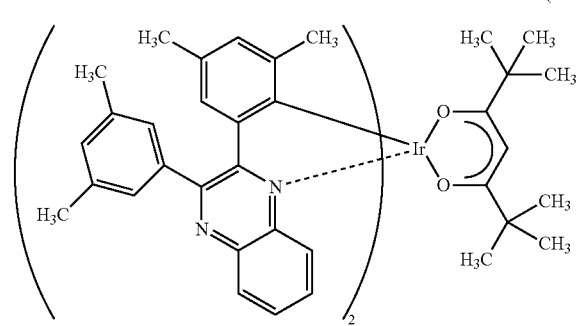
(100)

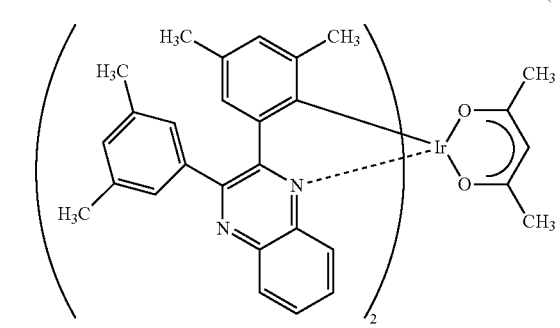
(101)

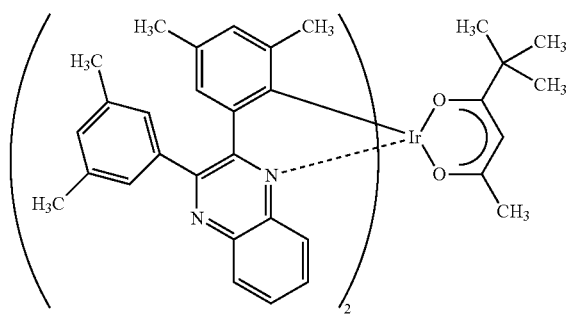
(102)
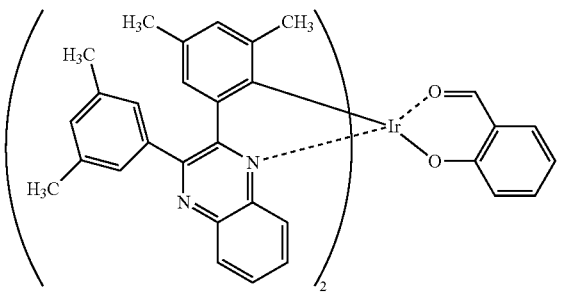
(107)
(103)
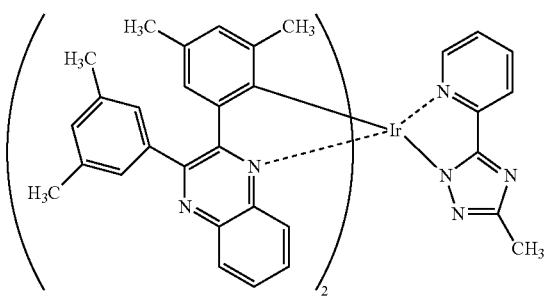
(108)
(104)
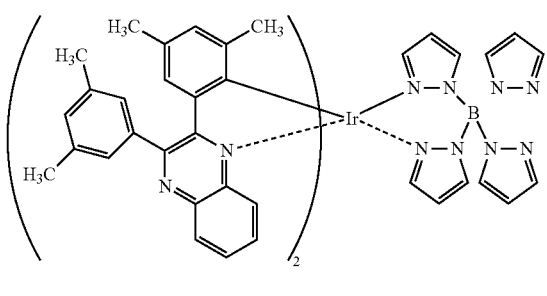
(109)
(105)
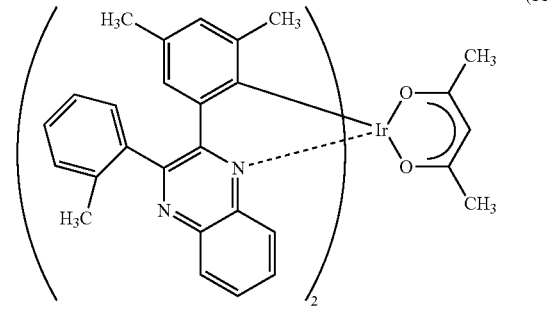
(110)
(106)
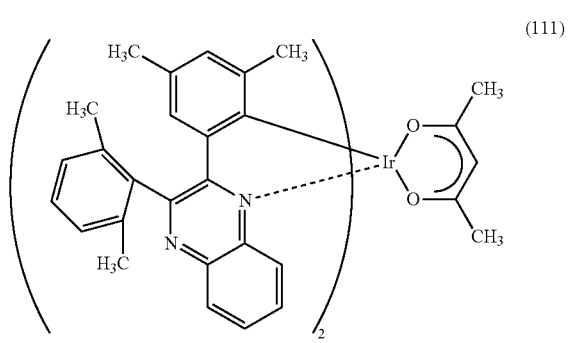
(111)

(112)
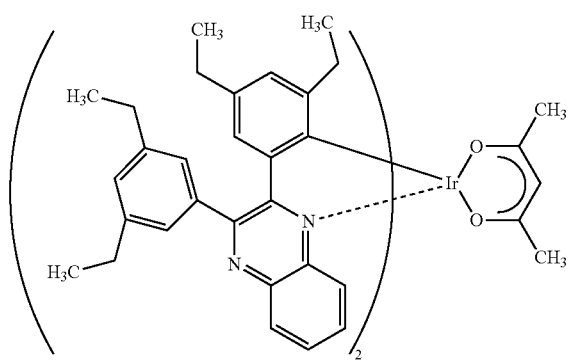
(113)
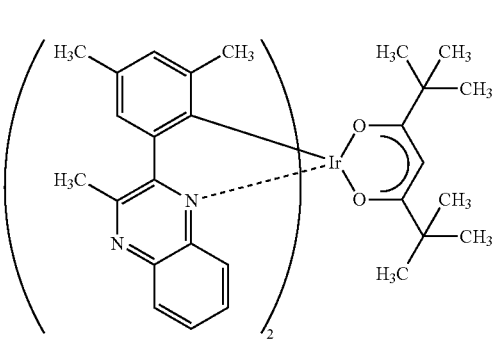
(114)
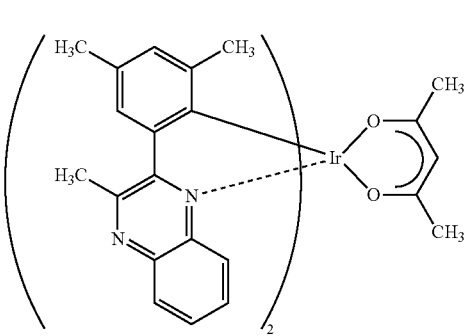
(115)
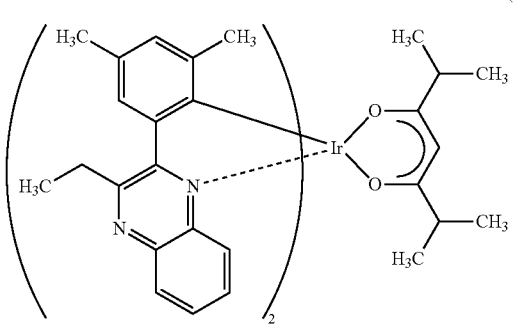
(116)
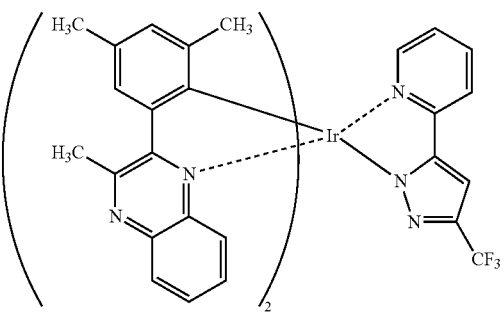
(117)
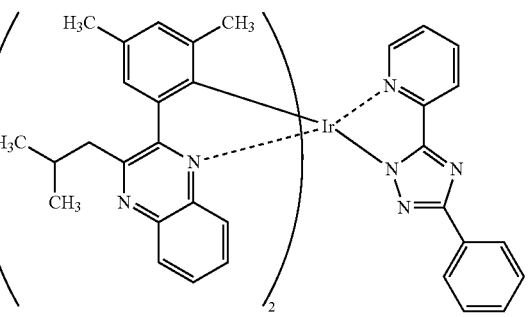
(118)
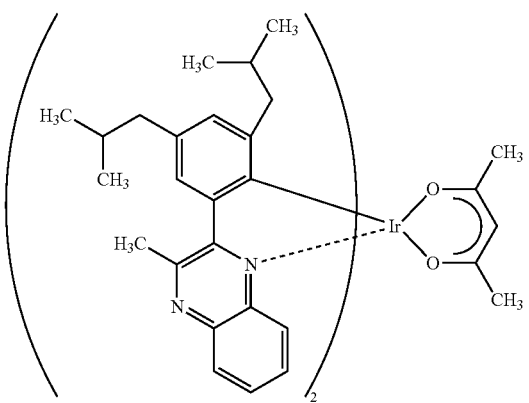
(119)
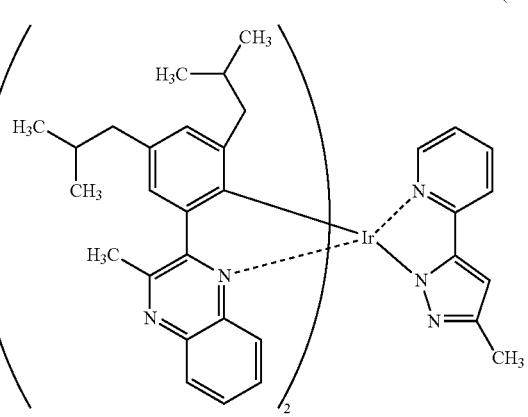

-continued

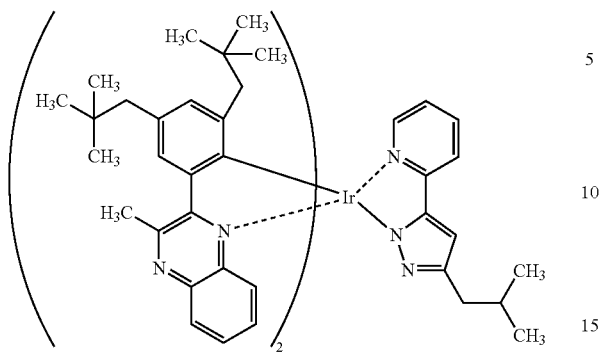

(120)

Note that organometallic iridium complexes represented by Structural Formulae (100) to (120) are novel substances that are capable of emitting phosphorescence. Note that there can be geometrical isomers and stereoisomers of these substances depending on the type of the ligand. The organometallic iridium complex of one embodiment of the present invention includes all of these isomers.

Next, an example of a method of synthesizing the organometallic iridium complex represented by General Formula (G1) is described.

<<Method of Synthesizing Quinoxaline Derivative Represented by General Formula (G0)>>

An example of a method of synthesizing the quinoxaline derivative represented by General Formula (G0) is described.

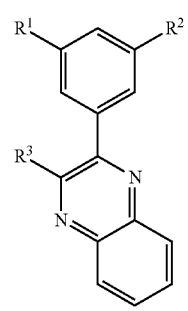

(G0)

Note that in General Formula (G0), $R^1$ to $R^3$ separately represent an alkyl group having 1 to 6 carbon atoms, a phenyl group, or a phenyl group having an alkyl group having 1 to 6 carbon atoms as a substituent.

Three Synthesis Schemes (A1), (A2), and (A3) of the quinoxaline derivative represented by General Formula (G0) are shown below.

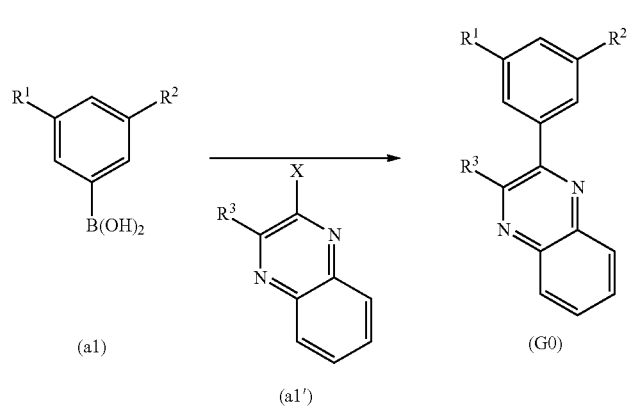

(A1)

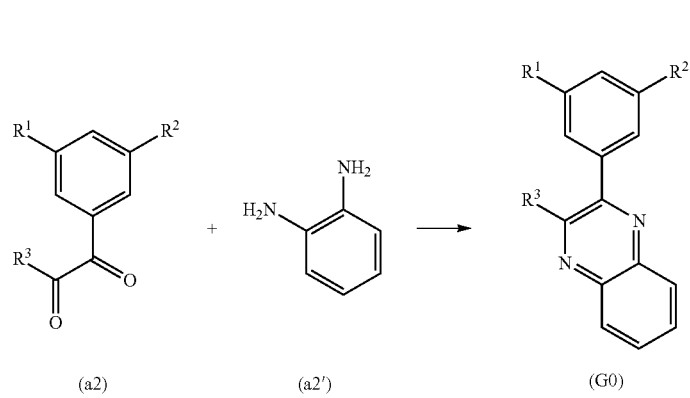

(A2)

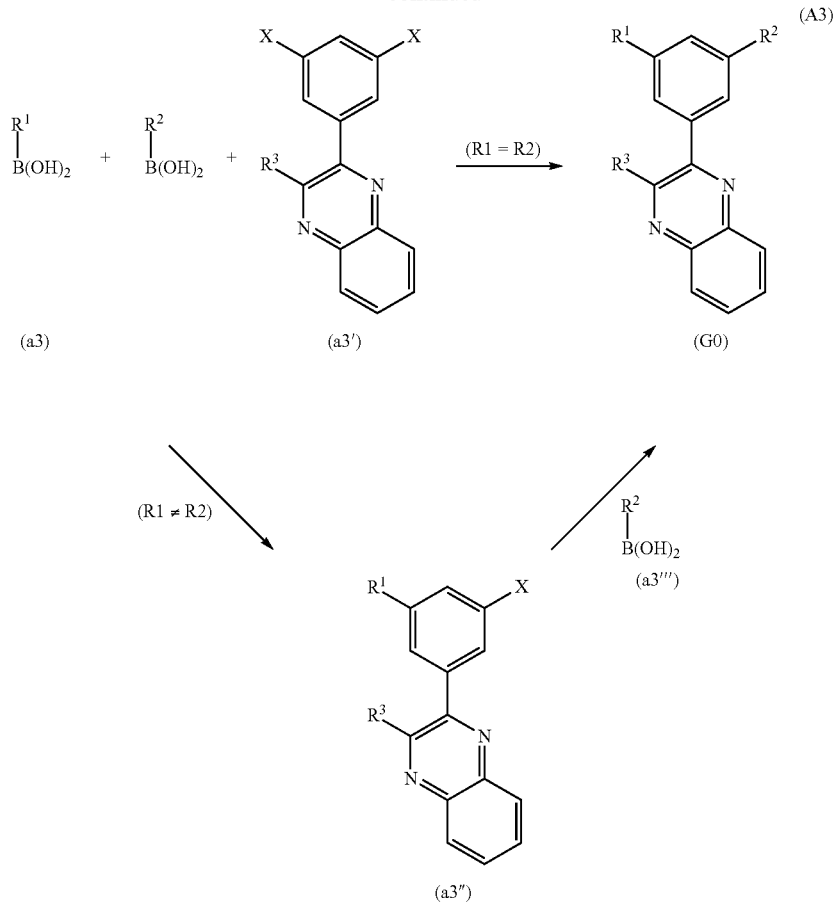

In Synthesis Scheme (A1), 3,5-dialkylphenyl boronic acid (a1) is coupled with a halogenated quinoxaline compound (a1') to obtain the quinoxaline derivative (G0).

In Synthesis Scheme (A2), α-diketone (a2) is reacted with o-phenylenediamine (a2') to obtain the quinoxaline derivative (G0).

In Synthesis Scheme (A3), in the case where $R^1$ and $R^2$ are the same alkyl group, alkyl boronic acid (a3) is coupled with a quinoxaline compound substituted with 3,5-dihalogenated phenyl (a3') to obtain the quinoxaline derivative (G0); meanwhile, in the case where $R^1$ and $R^2$ are different alkyl groups, a quinoxaline compound substituted with halogenated phenyl (a3") that is an intermediate of the quinoxaline compound substituted with halogenated phenyl is obtained first, and then the intermediate is coupled with alkyl boronic acid (a3'''), so that the quinoxaline derivative (G0) is obtained. Note that, in the formula, X represents a halogen element.

Other than the above-described three methods, there are a plurality of known methods of synthesizing the derivative (G0). Thus, any of the methods can be employed.

Since many kinds of the compounds (a1), (a1'), (a2), (a2'), (a3), (a3'), (a3"), and (a3''') in the schemes are commercially available or can be synthesized, many kinds of quinoxaline derivatives represented by General Formula (G0) can be synthesized. Thus, a feature of the organometallic iridium complex of one embodiment of the present invention is the abundance of ligand variations.

<<Method of Synthesizing Organometallic Iridium Complex of One Embodiment of the Present Invention Represented by General Formula (G1)>>

Next, a method of synthesizing the organometallic iridium complex of one embodiment of the present invention represented by General Formula (G1), which is formed using the quinoxaline derivative represented by General Formula (G0), is described.

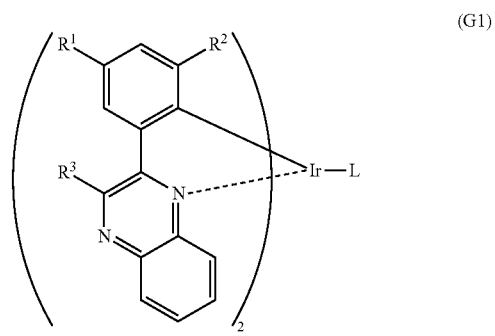

In General Formula (G1), $R^1$ to $R^3$ separately represent an alkyl group having 1 to 6 carbon atoms, a phenyl group, or a phenyl group having an alkyl group having 1 to 6 carbon atoms as a substituent. In addition, L represents a monoanionic ligand.

Synthesis Scheme (B) of the organometallic iridium complex represented by General Formula (G1) is shown below.

Iridium compound containing halogen +

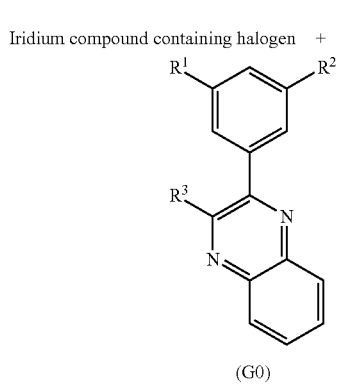

(G0)

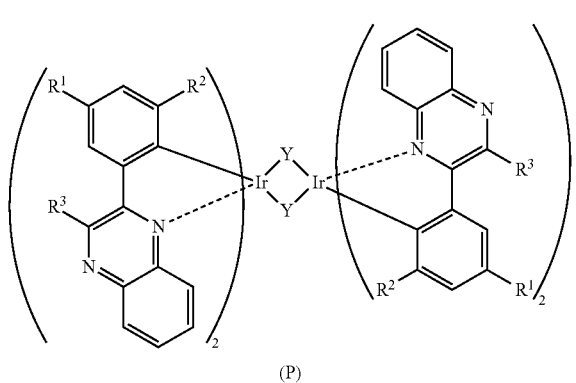

(P)

(B)

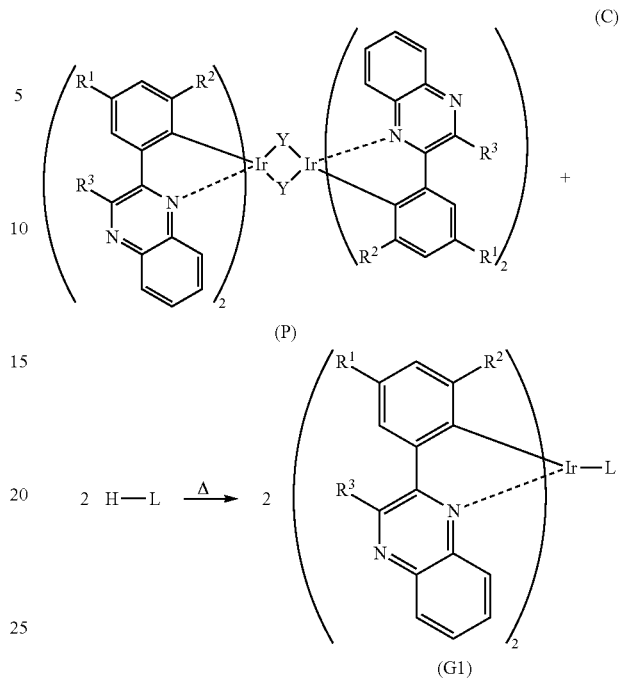

(C)

(G1)

In Synthesis Scheme (B), $R^1$ to $R^3$ separately represent an alkyl group having 1 to 6 carbon atoms, a phenyl group, or a phenyl group having an alkyl group having 1 to 6 carbon atoms as a substituent. In addition, Y represents a halogen.

As shown in Synthesis Scheme (B), the quinoxaline derivative represented by General Formula (G0) and an iridium compound containing a halogen (e.g., iridium chloride, iridium bromide, or iridium iodide) are heated in an inert gas atmosphere using no solvent, an alcohol-based solvent (e.g., glycerol, ethylene glycol, 2-methoxyethanol, or 2-ethoxyethanol) alone, or a mixed solvent of water and one or more of the alcohol-based solvents, whereby a dinuclear complex (P), which is one type of an organometallic iridium complex having a halogen-bridged structure, can be obtained.

There is no particular limitation on a heating means, and an oil bath, a sand bath, or an aluminum block may be used. Alternatively, microwaves can be used as a heating means.

Furthermore, as shown in Synthesis Scheme (C), the dinuclear complex (P) obtained in Synthesis Scheme (B) is reacted with a ligand HL in an inert gas atmosphere, whereby a proton of the ligand HL is eliminated and a monoanionic ligand L coordinates to iridium that is a central metal. Thus, the organometallic iridium complex of one embodiment of the present invention represented by General Formula (G1) can be obtained.

In Synthesis Scheme (C), $R^1$ to $R^3$ separately represent an alkyl group having 1 to 6 carbon atoms, a phenyl group, or a phenyl group having an alkyl group having 1 to 6 carbon atoms as a substituent. In addition, L represents a monoanionic ligand.

There is no particular limitation on a heating means, and an oil bath, a sand bath, or an aluminum block may be used. Alternatively, microwaves can be used as a heating means.

The example of a method of synthesizing the organometallic iridium complex of one embodiment of the present invention is described above; however, one embodiment of the present invention is not limited to the examples, and any other synthesis methods may be employed.

The above-described organometallic iridium complex of one embodiment of the present invention can emit phosphorescence and thus can be used as a light-emitting material or a light-emitting substance of a light-emitting element.

With the use of the organometallic iridium complex of one embodiment of the present invention, a light-emitting element, a light-emitting device, or a lighting device with high emission efficiency can be obtained. It is also possible to obtain a light-emitting element, a light-emitting device, or a lighting device with low power consumption.

Note that the structure described in this embodiment can be combined as appropriate with any of the structures described in the other embodiments.

Embodiment 2

In this embodiment, a light-emitting element in which the organometallic iridium complex described in Embodiment 1 as one embodiment of the present invention is used for a light-emitting layer is described with reference to FIG. 1.

In a light-emitting element described in this embodiment, as illustrated in FIG. 1, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge-generation layer (E) 116, and the like in addition to the light-emitting layer 113.

By application of voltage to such a light-emitting element, holes injected from the first electrode 101 side and electrons injected from the second electrode 103 side recombine in the light-emitting layer 113 to raise the organometallic iridium complex to an excited state. Then, light is emitted when the organometallic iridium complex in the excited state relaxes to the ground state. Thus, the organometallic iridium complex in one embodiment of the present invention functions as a light-emitting substance in the light-emitting element.

The hole-injection layer 111 included in the EL layer 102 contains a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge-generation layer (E) 116 contains a substance having a high hole-transport property and an acceptor substance. Electrons are extracted from the substance having a high hole-transport property owing to the acceptor substance, and the extracted electrons are injected from the electron-injection layer 115 having an electron-injection property into the light-emitting layer 113 through the electron-transport layer 114.

A specific example in which the light-emitting element described in this embodiment is fabricated is described.

As the first electrode (anode) 101 and the second electrode (cathode) 103, a metal, an alloy, an electrically conductive compound, a mixture thereof, and the like can be used. Specifically, indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method, an evaporation method (e.g., a vacuum evaporation method), or the like.

Examples of the substance having a high hole-transport property used for the hole-injection layer 111, the hole-transport layer 112, and the charge-generation layer (E) 116 include aromatic amine compounds such as 4,4'-bis[N-(1-naphthyl)-N-phenylamino]biphenyl (abbreviation: NPB or a-NPD), N,N'-bis(3-methylphenyl)-N,N-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). Other examples include 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-Carbazole (abbreviation: CzPA). The substances given here are mainly ones that have a hole mobility of $10^{-6}$ $cm^2/Vs$ or higher. Note that any substance other than the substances given above may also be used as long as the hole-transport property is higher than the electron-transport property.

Other examples include a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD).

Examples of the acceptor substance that is used for the hole-injection layer 111 and the charge-generation layer (E) 116 include oxides of metals belonging to any of Group 4 to Group 8 of the periodic table. Specifically, molybdenum oxide is particularly preferable.

The light-emitting layer 113 contains any of the organometallic iridium complexes described in Embodiment 1 as a guest material serving as a light-emitting substance and a substance that has higher triplet excitation energy than this organometallic iridium complex as a host material.

Preferable examples of the substance (i.e., host material) used for dispersing any of the above-described organometallic iridium complexes include compounds having an arylamine skeleton, such as 2,3-bis(4-diphenylaminophenyl)quinoxaline (abbreviation: TPAQn) and NPB; carbazole derivatives such as CBP and 4,4',4"-tris(carbazol-9-yl)triphenylamine (abbreviation: TCTA); and metal complexes such as bis[2-(2-hydroxyphenyl)pyridinato]zinc (abbreviation: $Znpp_2$), bis[2-(2-hydroxyphenyl)benzoxazolato]zinc (abbreviation: $Zn(BOX)_2$), bis(2-methyl-8-quinolinolato)(4-phenylphenolato)aluminum (abbreviation: BAlq), and tris(8-quinolinolato)aluminum (abbreviation: $Alq_3$). Alternatively, a high molecular compound such as PVK can be used.

Note that in the case where the light-emitting layer 113 contains the above-described organometallic iridium complex (guest material) and the host material, phosphorescence with high emission efficiency can be obtained from the light-emitting layer 113.

The electron-transport layer 114 is a layer containing a substance having a high electron-transport property. For the electron-transport layer 114, a metal complex such as $Alq_3$, tris(4-methyl-8-quinolinolato)aluminum (abbreviation: $Almq_3$), bis(10-hydroxybenzo[h]quinolinato)beryllium(II) (abbreviation: $BeBq_2$), BAlq, $Zn(BOX)_2$, or bis[2-(2-hydroxyphenyl)benzothiazolato]zinc(II) (abbreviation: $Zn(BTZ)_2$) can be used. A heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can also be used. The substances given here are mainly ones that have an electron mobility of $10^{-6}$ cm$^2$/Vs or higher. Note that any substance other than the substances given above may be used for the electron-transport layer 114 as long as the electron-transport property is higher than the hole-transport property.

The electron-transport layer 114 is not limited to a single layer, and may be a stack of two or more layers containing any of the substances given above.

The electron-injection layer 115 contains a substance having a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. Any of the above substances for forming the electron-transport layer 114 can also be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, an alkali metal oxide or an alkaline earth metal oxide is preferable, and lithium oxide, calcium oxide, and barium oxide are given. Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, electron-injection layer 115, and charge-generation layer (E) 116 can be formed by a method such as an evaporation method (e.g., a vacuum evaporation method), an ink-jet method, or a coating method.

In the above-described light-emitting element, current flows because of a potential difference applied between the first electrode 101 and the second electrode 103 and holes and electrons are recombined in the EL layer 102, whereby light is emitted. Then, the emitted light is extracted outside through one or both of the first electrode 101 and the second electrode 103. Thus, one or both of the first electrode 101 and the second electrode 103 are electrodes having light-transmitting properties.

The above-described light-emitting element can emit phosphorescence originating from the organometallic iridium complex and thus can have higher efficiency than a light-emitting element using a fluorescent compound.

Note that the structure described in this embodiment can be combined as appropriate with any of the structures described in the other embodiments.

Embodiment 3

In this embodiment, as one embodiment of the present invention, a light-emitting element in which two or more kinds of organic compounds as well as an organometallic iridium complex are used for a light-emitting layer is described.

Figure 2:
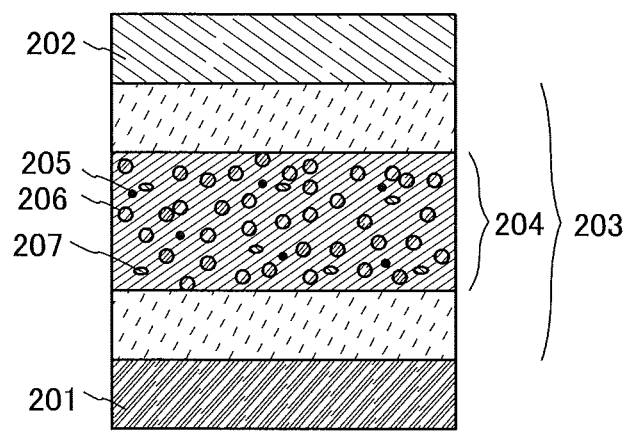
FIG. 2 illustrates a structure of a light-emitting element.

A light-emitting element described in this embodiment includes an EL layer 203 between a pair of electrodes (an anode 201 and a cathode 202) as illustrated in FIG. 2. Note that the EL layer 203 includes at least a light-emitting layer 204 and may include a hole-injection layer, a hole-transport layer, an electron-transport layer, an electron-injection layer, a charge-generation layer (E), and the like. Note that for the hole-injection layer, the hole-transport layer, the electron-transport layer, the electron-injection layer, and the charge-generation layer (E), the substances given in Embodiment 2 can be used.

The light-emitting layer 204 described in this embodiment contains a phosphorescent compound 205 using the organometallic iridium complex described in Embodiment 1, a first organic compound 206, and a second organic compound 207. Note that the phosphorescent compound 205 is a guest material in the light-emitting layer 204. One of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. In addition, it is possible to suppress concentration quenching due to high concentration of the guest material, and thus the light-emitting element can have higher emission efficiency.

Note that it is preferable that the triplet excitation energy level ($T_1$ level) of each of the first organic compound 206 and the second organic compound 207 be higher than that of the phosphorescent compound 205. This is because, when the $T_1$ level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency is decreased.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (fluorescence spectrum in energy transfer from a singlet excited state, phosphorescence spectrum in energy transfer from a triplet excited state) largely overlap with an absorption spectrum of a guest material (specifically, spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side as compared to the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side; thus, the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of the host material.

Thus, in this embodiment, a combination of the first organic compound 206 and the second organic compound 207 preferably forms an exciplex (also referred to as excited complex). In this case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex that is located on the longer wavelength side. Moreover, when the first organic compound 206 and the second organic compound 207 are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is assumed to occur.

For the phosphorescent compound 205, the organometallic iridium complex described in Embodiment 1 is used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

Examples of the compound that easily accepts electrons include 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl) phenyl]dibenzo[f,h]quinoxaline (abbreviation: 7mDBTPDBq-II), and 6-[3-(dibenzothiophen-4-yl)phenyl] dibenzo[f,h]quinoxaline (abbreviation: 6mDBTPDBq-II).

Examples of the compound that easily accepts holes include 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenyl-carbazol-3-yl)-N,N'-diphenylbenzene-1,3-diamine (abbreviation: PCA2B), N-(9,9-dimethyl-2-N,N'-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis [N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

The above-described first and second organic compounds 206 and 207 are not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound. Thus, high external quantum efficiency of the light-emitting element can be achieved.

Note that in another structure of one embodiment of the present invention, the light-emitting layer 204 can be formed using a host molecule having a hole-trapping property and a host molecule having an electron-trapping property as the two kinds of organic compounds (the first organic compound 206 and the second organic compound 207) other than the phosphorescent compound 205 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above compounds that easily accept holes and the above compounds that easily accept electrons.

The structure of the light-emitting element described in this embodiment is an example. The light-emitting element of one embodiment of the present invention can have a microcavity structure in addition to the structure.

Note that the structure described in this embodiment can be combined as appropriate with any of the structures described in the other embodiments.

Embodiment 4

In this embodiment, as one embodiment of the present invention, a light-emitting element (hereinafter referred to as tandem light-emitting element) in which a charge-generation layer is provided between a plurality of EL layers is described.

Figure 3A:
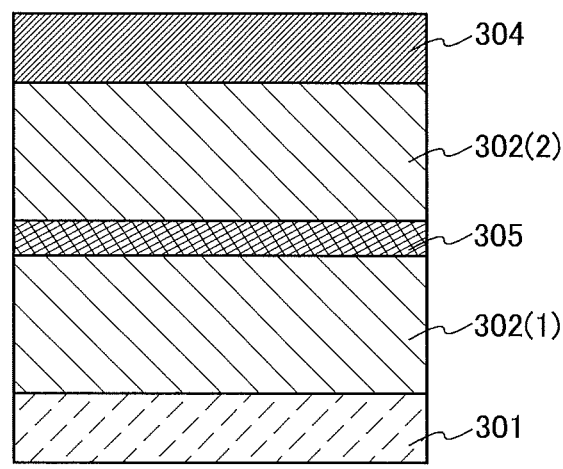
FIGS. 3A and 3B each illustrate a structure of a light-emitting element.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those described in Embodiment 2. In addition, although the plurality of EL layers (the first EL layer 302(1) and the second EL layer 302(2)) may have a structure similar to that of the EL layer described in Embodiment 2 or 3, any of the EL layers may have a structure similar to that of the EL layer described in Embodiment 2 or 3. In other words, the structures of the first EL layer 302(1) and the second EL layer 302(2) may be the same or different from each other and can be similar to those of the EL layers described in Embodiment 2 or 3.

In addition, a charge-generation layer (I) 305 is provided between the plurality of EL layers (the first EL layer 302(1) and the second EL layer 302(2)). The charge-generation layer (I) 305 has a function of injecting electrons into one of the EL layers and injecting holes into the other of the EL layers when voltage is applied between the first electrode 301 and the second electrode 304. In this embodiment, when voltage is applied such that the potential of the first electrode 301 is higher than that of the second electrode 304, the charge-generation layer (I) 305 injects electrons into the first EL layer 302(1) and injects holes into the second EL layer 302(2).

Note that in terms of light extraction efficiency, the charge-generation layer (I) 305 preferably has a light-transmitting property with respect to visible light (specifically, the charge-generation layer (I) 305 has a visible light transmittance of 40% or more). The charge-generation layer (I) 305 functions even if it has lower conductivity than the first electrode 301 or the second electrode 304.

The charge-generation layer (I) 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, the organic compound having a high hole-transport property can be, for example, an aromatic amine compound such as NPB, TPD, TDATA, MTDATA, or BSPB, or the like. The substances given here are mainly ones that have a hole mobility of $10^{-6}$ cm$^2$/Vs or higher. Note that any substance other than the substances given above may be used as long as the hole-transport property is higher than the electron-transport property.

As the electron acceptor, 7,7,8,8-tetracyano-2,3,5,6-tetrafluoroquinodimethane (abbreviation: F$_4$-TCNQ), chloranil, and the like can be given. Specifically, it is preferable to use vanadium oxide, niobium oxide, tantalum oxide, chromium oxide, molybdenum oxide, tungsten oxide, manganese oxide, and rhenium oxide because of their high electron accepting properties. Among these, molybdenum oxide is especially preferable because it is stable in the air, has a low hygroscopic property, and is easy to handle.

In the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. A metal complex having an oxazole-based ligand or a thiazole-based ligand, such as Zn(BOX)$_2$ or Zn(BTZ)$_2$ can also be used. It is also possible to use PBD, OXD-7, TAZ, Bphen, BCP, or the like instead of such a metal complex. The substances given here are mainly ones that have an electron mobility of $10^{-6}$ cm$^2$/Vs or higher. Note that any substance other than the substances given above may be used as long as the electron-transport property is higher than the hole-transport property.

As the electron donor, it is possible to use an alkali metal, an alkaline earth metal, a rare earth metal, a metal belonging to Group 2 to Group 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may also be used as the electron donor.

Note that forming the charge-generation layer (I) 305 by using any of the above materials can suppress an increase in drive voltage caused by the stack of the EL layers.

Figure 3B:
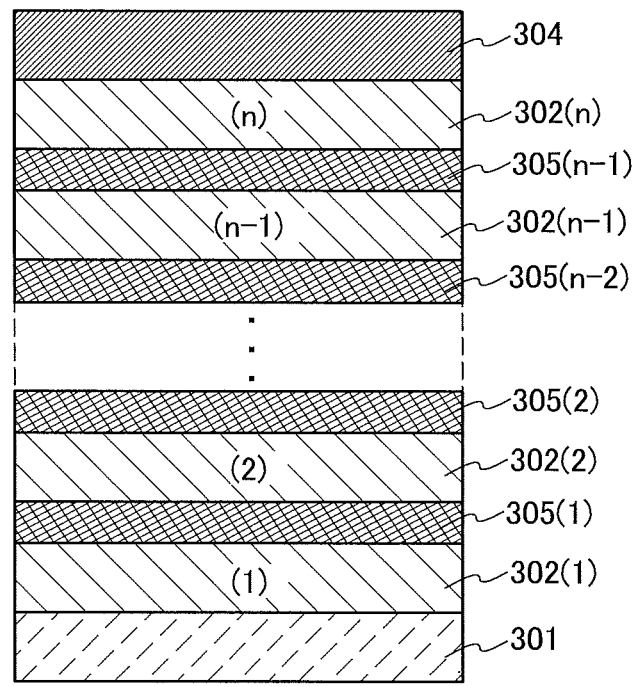

Although the light-emitting element including two EL layers is described in this embodiment, the present invention can be similarly applied to a light-emitting element in which n EL layers (302(1) to 302(n)) (n is three or more) are stacked as illustrated in FIG. 3B. In the case where a plurality of EL layers are included between a pair of electrodes as in the light-emitting element according to this embodiment, by providing charge-generation layers (I) (305(1) to 305(n−1)) between the EL layers, light emission in a high luminance region can be obtained with current density kept low. Since the current density can be kept low, the element can have a long lifetime. When the light-emitting element is used for light-emitting devices, and lighting devices each having a large light-emitting area, voltage drop due to resistance of an electrode material can be reduced, thereby achieving uniform light emission in a large area.

When the EL layers have different emission colors, a desired emission color can be obtained from the whole light-emitting element. For example, in the light-emitting element having two EL layers, when an emission color of the first EL layer and an emission color of the second EL layer are made to be complementary colors, a light-emitting element emitting white light as a whole light-emitting element can also be obtained. Note that "complementary colors" refer to colors that can produce an achromatic color when combined. In other words, combination of complementary colors allows white light emission to be obtained.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 5

In this embodiment, a light-emitting device that includes a light-emitting element in which the organometallic iridium complex of one embodiment of the present invention is used in a light-emitting layer is described.

The light-emitting device may be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 4A and 4B.

Figure 4A:
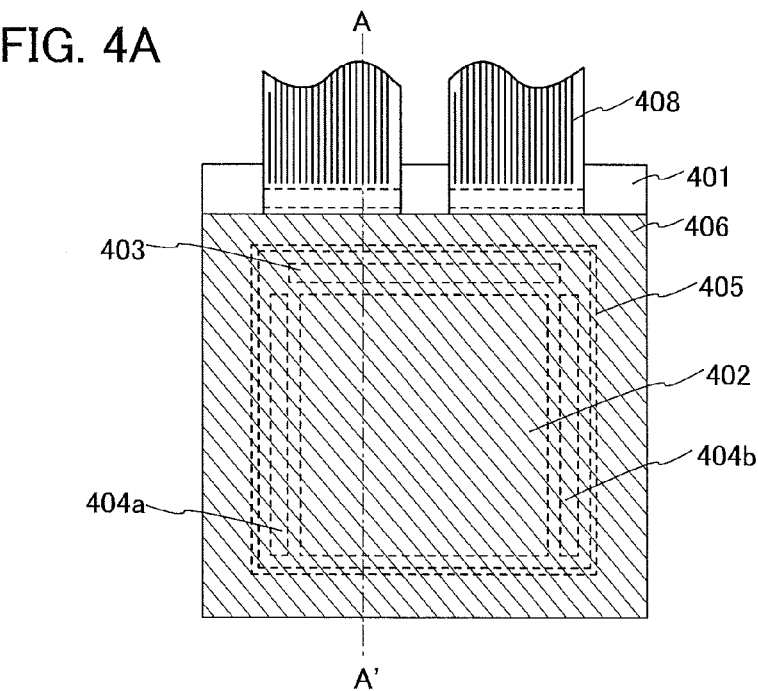
FIGS. 4A and 4B illustrate a light-emitting device.
Figure 4B:
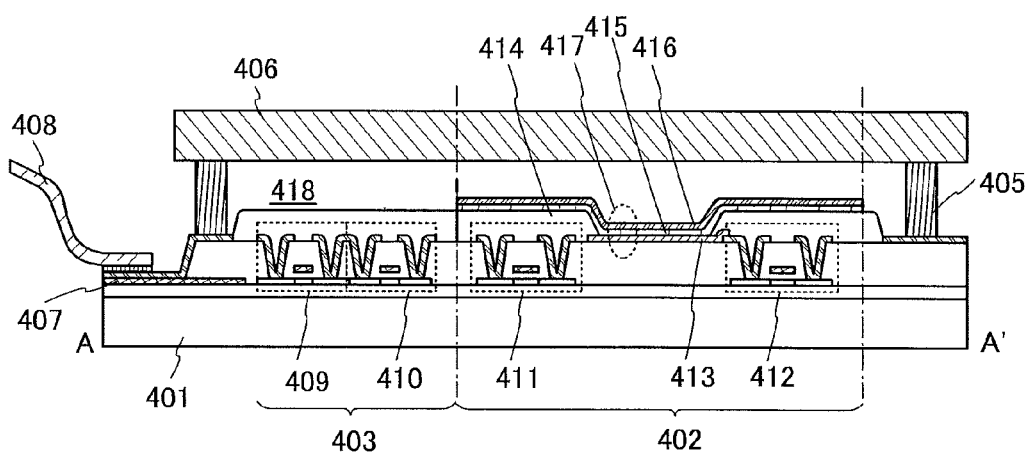

FIG. 4A is a top view illustrating a light-emitting device and FIG. 4B is a cross-sectional view taken along the chain line A-A' in FIG. 4A. The active matrix light-emitting device of this embodiment includes a pixel portion 402 provided over an element substrate 401, a driver circuit portion (a source line driver circuit) 403, and driver circuit portions (gate line driver circuits) 404a and 404b. The pixel portion 402, the driver circuit portion 403, and the driver circuit portions 404a and 404b are sealed with a sealant 405 between the element substrate 401 and a sealing substrate 406.

In addition, over the element substrate 401, a lead wiring 407 for connecting an external input terminal, through which a signal (e.g., a video signal, a clock signal, a start signal, or a reset signal) or an electric potential is transmitted to the driver circuit portion 403 and the driver circuit portions 404a and 404b, is provided. Here, an example is described in which a flexible printed circuit (FPC) 408 is provided as the external input terminal. Although only the FPC is shown here, the FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 4B. The driver circuit portion and the pixel portion are formed over the element substrate 401; here are illustrated the driver circuit portion 403 that is the source line driver circuit and the pixel portion 402.

The driver circuit portion 403 is an example where a CMOS circuit is formed, which is a combination of an n-channel FET 409 and a p-channel FET 410. Note that a circuit included in the driver circuit portion may be formed using various CMOS circuits, PMOS circuits, or NMOS circuits. Any of a staggered type FET and a reverse-staggered type FET may be used. Furthermore, the crystallinity of a semiconductor film used in the FET is not limited and may be amorphous or crystalline. Examples of a semiconductor material include Group IV semiconductors (e.g., silicon and gallium), compound semiconductors (including oxide semiconductors), and organic semiconductors. Although a driver integrated type in which the driver circuit is formed over the substrate is described in this embodiment, the driver circuit is not necessarily be formed over the substrate, and the driver circuit can be formed outside, not over the substrate.

The pixel portion 402 is formed of a plurality of pixels each of which includes a switching FET 411, a current control FET 412, and a first electrode (anode) 413 electrically connected to a wiring (a source electrode or a drain electrode) of the current control FET 412. An insulator 414 is formed to cover an end portion of the first electrode (anode) 413.

The insulator 414 preferably has a curved surface with curvature at an upper end portion or a lower end portion thereof in order to obtain favorable coverage by a film that is to be stacked over the insulator 414. For example, the insulator 414 can be formed using either a negative photosensitive resin or a positive photosensitive resin. The material of the insulator 414 is not limited to an organic compound and an inorganic compound such as silicon oxide or silicon oxynitride can also be used.

An EL layer 415 and a second electrode (cathode) 416 are stacked over the first electrode (anode) 413. The EL layer 415 is provided with at least a light-emitting layer in which the organometallic iridium complex of one embodiment of the present invention can be used. In addition to the light-emitting layer, a hole-injection layer, a hole-transport layer, an electron-transport layer, an electron-injection layer, a charge-generation layer, and the like can be provided as appropriate in the EL layer 415.

A light-emitting element 417 is formed of a stacked structure of the first electrode (anode) 413, the EL layer 415, and the second electrode (cathode) 416. For the first electrode (anode) 413, the EL layer 415, and the second electrode (cathode) 416, the materials described in Embodiment 2 can be used. Although not illustrated, the second electrode (cathode) 416 is electrically connected to the FPC 408 that is an external input terminal.

Although the cross-sectional view of FIG. 4B illustrates only one light-emitting element 417, a plurality of light-emitting elements are arranged in matrix in the pixel portion 402. Light-emitting elements that emit light of three kinds of colors (R, G, and B) are selectively formed in the pixel portion 402, whereby a light-emitting device capable of full color display can be obtained. Alternatively, a light-emitting device capable of full color display may be fabricated by a combination with color filters.

In addition, the sealing substrate 406 is attached to the element substrate 401 with the sealant 405, so that a light-emitting element 417 is provided in a space 418 surrounded by the element substrate 401, the sealing substrate 406, and the sealant 405. Note that the space 418 may be filled with an inert gas (e.g., nitrogen or argon) or the sealant 405.

Note that an epoxy-based resin or glass frit is preferably used as the sealant 405. It is preferable that such a material do not transmit moisture or oxygen as much as possible. As the sealing substrate 406, a glass substrate, a quartz substrate, or a plastic substrate formed of fiber-reinforced plastic (FRP), poly(vinyl fluoride) (PVF), a polyester, an acrylic resin, or the like can be used. In the case where glass frit is used as the sealant, the element substrate 401 and the sealing substrate 406 are preferably glass substrates in terms of adhesion.

As described above, an active matrix light-emitting device can be obtained.

Note that the structure described in this embodiment can be combined as appropriate with any of the structures described in the other embodiments.

Embodiment 6

In this embodiment, examples of a lighting device in which a light-emitting device including the organometallic iridium complex of one embodiment of the present invention is used are described with reference to FIG. 5.

Figure 5:
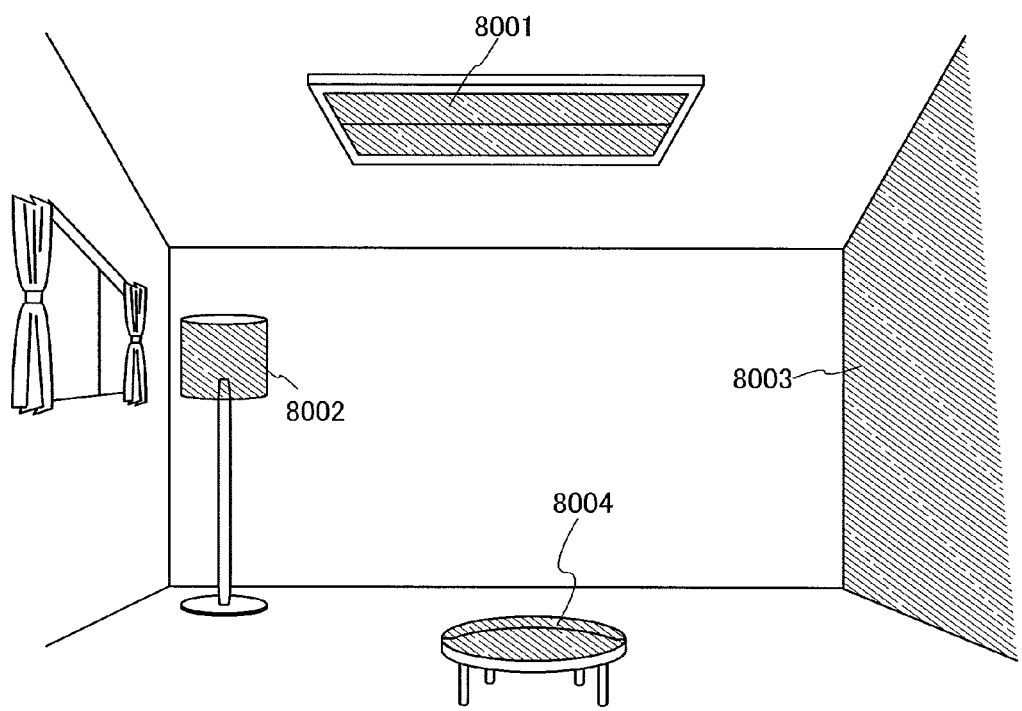
FIG. 5 illustrates lighting devices.

FIG. 5 illustrates an example in which the light-emitting device is used as an indoor lighting device 8001. Since the light-emitting device can have a large area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. A wall of the room may be provided with a large-sized lighting device 8003.

In addition, when the light-emitting device is used for a table by being used as a surface of a table, a lighting device 8004 which has a function as a table can be obtained. When the light-emitting device is used as part of other furniture, a lighting device which has a function as the furniture can be obtained.

As described above, a variety of lighting devices in which the light-emitting device is used can be obtained. Note that these lighting devices are also embodiments of the present invention.

Note that the structure described in this embodiment can be combined as appropriate with any of the structures described in the other embodiments.

Example 1

Synthesis Example 1

In this example, a method of synthesizing bis{4,6-dimethyl-2-[3-(3,5-dimethylphenyl)-2-quinoxalinyl-κN]phenyl-κC}(2,2',6,6'-tetramethyl-3,5-heptanedionato-κ$^2$O,O') iridium(III) (abbreviation: [Ir(dmdpq)$_2$(dpm)]) that is an organometallic iridium complex of one embodiment of the present invention and is represented by Structural Formula (100) in Embodiment 1 is described. A structure of [Ir(dmdpq)$_2$(dpm)] is shown below.

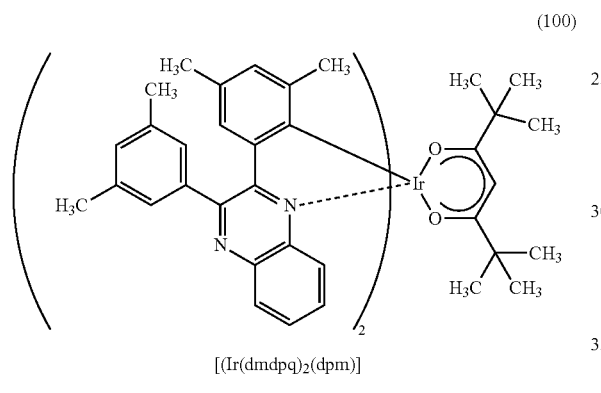

[(Ir(dmdpq)$_2$(dpm)]  (100)

Step 1: Synthesis of 2,3-bis(3,5-dimethylphenyl)quinoxaline (abbreviation: Hdmdpq)

First, 1.2 g of o-phenylenediamine, 3.0 g of 3,3',5,5'-tetramethylbenzyl, and 30 mL of ethanol were put in a 200-mL three-neck flask, and the air in the flask was replaced with nitrogen. After that, the mixture was heated at 90° C. for 7.5 hours to cause a reaction. Water was added to the reacted solution, and the organic layer was extracted with dichloromethane. The obtained organic layer was washed with water and saturated saline, and was dried with magnesium sulfate. The solution obtained by the drying was filtered. The solvent in this solution was distilled off, and the obtained residue was dissolved in toluene and filtered through a filter aid in which Celite, alumina, and Celite were stacked in this order to give a quinoxaline derivative Hdmdpq that was a target substance as white powder in a yield of 87%. Synthesis Scheme (a-1) of Step 1 is shown below.

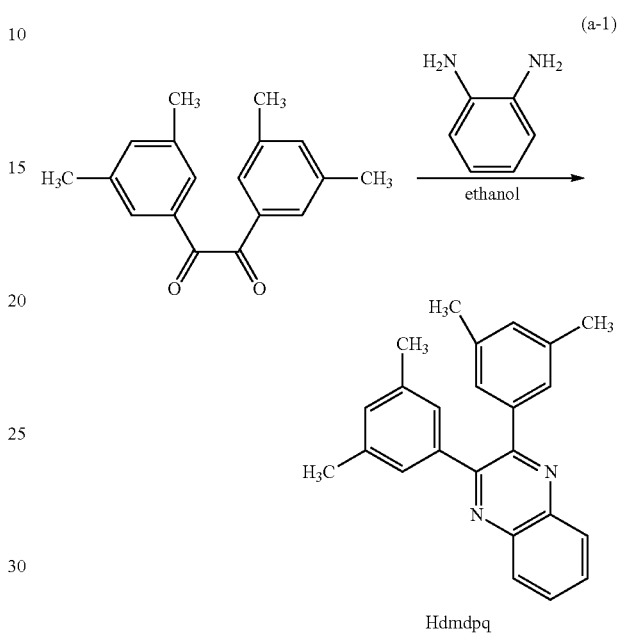

(a-1)

Hdmdpq

Step 2: Synthesis of di-μ-chloro-tetrakis{4,6-dimethyl-2-[3-(3,5-dimethylphenyl)-2-quinoxalinyl-κ,N]phenyl-κC}diiridium(III) (abbreviation: [Ir(dmdpq)$_2$Cl]$_2$)

Next, 15 mL of 2-ethoxyethanol, 5 mL of water, 1.08 g of Hdmdpq obtained in Step 1, and 0.48 g of iridium chloride hydrate (IrCl$_3$.H$_2$O) (produced by Sigma-Aldrich Corporation) were put in a recovery flask equipped with a reflux pipe, and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex [Ir(dmdpq)$_2$Cl]$_2$ as brown powder in a yield of 68%. Synthesis Scheme (a-2) of Step 2 is shown below.

(a-2)

2 IrCl$_3$·H$_2$O + 4 [Hdmdpq structure] → (2-ethoxyethanol/H$_2$O)

Hdmdpq

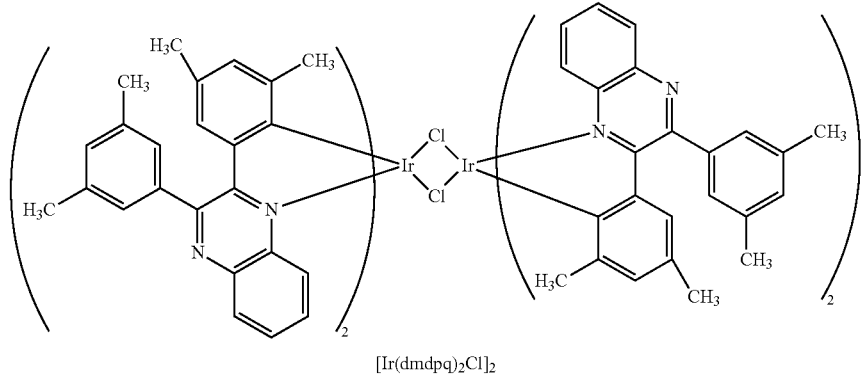

[Ir(dmdpq)₂Cl]₂

Step 3: Synthesis of bis{4,6-dimethyl-2-[3-(3,5-dimethylphenyl)-2-quinoxalinyl-κN]phenyl-κC}(2,2',6,6'-tetramethyl-3,5-heptanedionato-κ²O,O')iridium(III) (abbreviation: [Ir(dmdpq)₂(dpm)])

Furthermore, 30 mL of 2-ethoxyethanol, 0.98 g of [Ir(dmdpq)₂Cl]₂ that was the dinuclear complex obtained in Step 2, 0.16 g of dipivaloylmethane (abbreviation: Hdpm), and 0.57 g of sodium carbonate were put in a recovery flask equipped with a reflux pipe, and the air in the flask was replaced with argon. After that, the mixture was heated by irradiation with microwaves (2.45 GHz, 120 W) for 60 minutes. Here, 0.16 g of Hdpm was further added, and heating was performed by irradiation with microwaves (2.45 GHz, 120 W) for 60 minutes. Water was added to the reacted solution, and the organic layer was extracted with dichloromethane. The obtained organic layer was washed with water and saturated saline, and was dried with magnesium sulfate. The solution obtained by the drying was filtered. This solution was distilled off, and then the obtained residue was purified by flash column chromatography using dichloromethane as a developing solvent to give [Ir(dmdpq)₂(dpm)], which is the organometallic iridium complex of one embodiment of the present invention, as brown powder in a yield of 6%. Synthesis Scheme (a-3) of Step 3 is shown below.

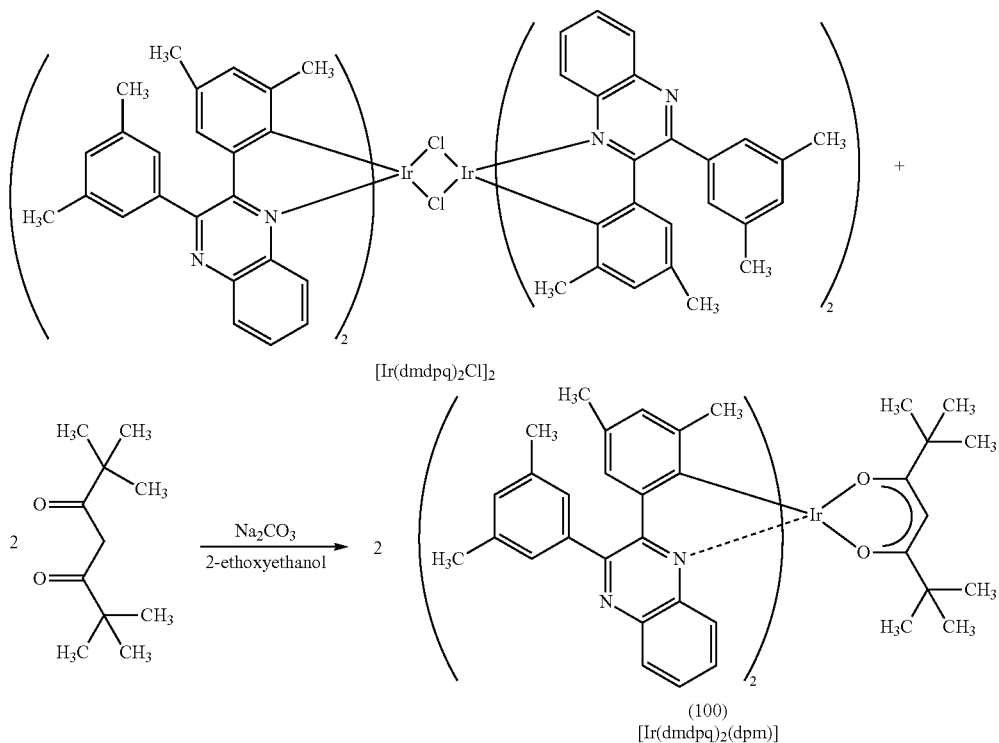

(a-3)

Figure 6:
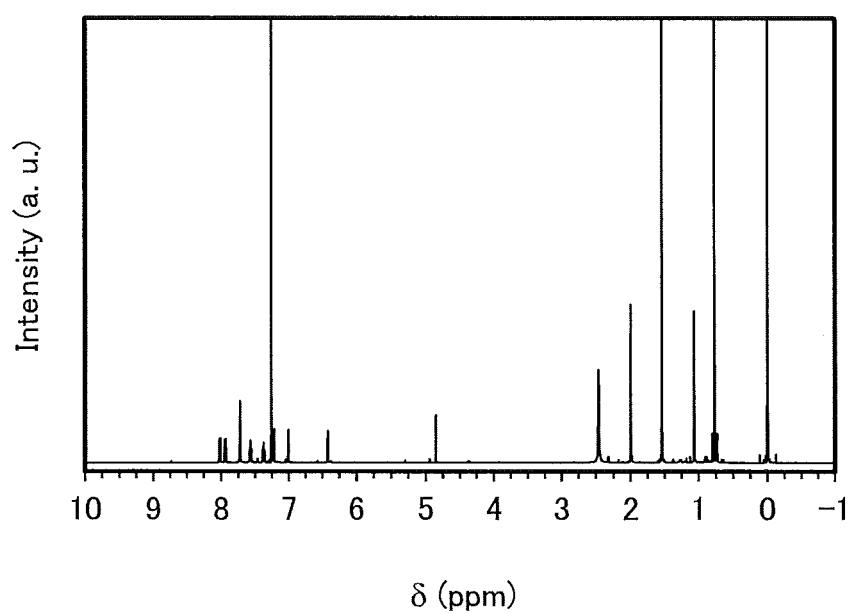
FIG. 6 is a $^1$H-NMR chart of an organometallic iridium complex represented by Structural Formula (100).

Results of analysis of the brown powder obtained in Step 3 by nuclear magnetic resonance spectrometry ($^1$H-NMR) are shown below. FIG. 6 is the $^1$H-NMR chart. The results demonstrate that [Ir(dmdpq)₂(dpm)], which is the organometallic iridium complex of one embodiment of the present invention and is represented by Structural Formula (100), was obtained in Synthesis Example 1.

$^1$H-NMR. δ (CDCl$_3$): 0.77 (s, 18H), 1.07 (s, 6H), 2.00 (s, 6H), 2.46 (s, 12H), 4.85 (s, 1H), 6.42 (s, 2H), 7.01 (s, 2H), 7.22 (s, 2H), 7.38 (t, 2H), 7.57 (t, 2H), 7.72 (s, 4H), 7.94 (d, 2H), 8.02 (d, 2H).

Figure 7:
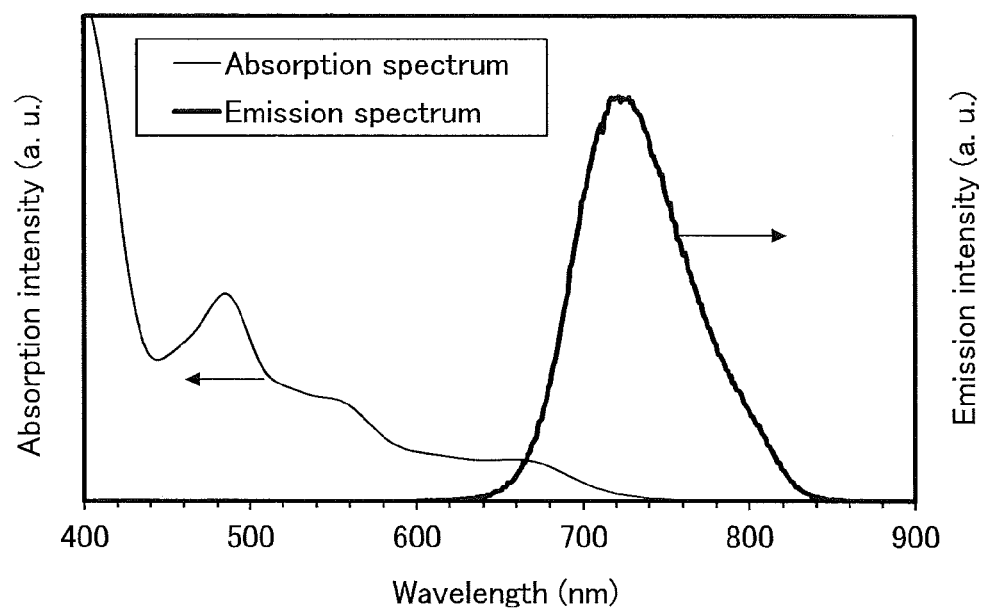
FIG. 7 shows an ultraviolet-visible absorption spectrum and an emission spectrum of the organometallic iridium complex represented by Structural Formula (100).

Next, an ultraviolet-visible absorption spectrum (hereinafter, simply referred to as an absorption spectrum) and an emission spectrum of [Ir(dmdpq)$_2$(dpm)] in a dichloromethane solution were measured. The absorption spectrum was measured with an ultraviolet-visible light spectrophotometer (V550 type, produced by JASCO Corporation) at room temperature in the state where the dichloromethane solution (0.063 mmol/L) was in a quartz cell. In addition, the measurement of the emission spectrum was conducted at room temperature, for which a fluorescence spectrophotometer (FS920 manufactured by Hamamatsu Photonics K.K.) was used and the degassed dichloromethane solution (0.063 mmol/L) was put in a quartz cell. FIG. 7 shows measurement results of the absorption spectrum and emission spectrum. The horizontal axis represents wavelength and the vertical axes represent absorption intensity and emission intensity. In FIG. 7, two solid lines are shown: a thin line represents the absorption spectrum, and a thick line represents the emission spectrum. The absorption spectrum shown in FIG. 7 was obtained by subtraction of the absorption spectra of the dichloromethane and the quartz from the obtained absorption spectrum.

As shown in FIG. 7, [Ir(dmdpq)$_2$(dpm)] that is the organometallic iridium complex of one embodiment of the present invention has an absorption peak at 475 nm and an emission peak at 722 nm. In addition, deep red light emission was observed in the dichloromethane solution.

Next, [Ir(dmdpq)$_2$(dpm)] obtained in this example was subjected to a MS analysis by liquid chromatography mass spectrometry (LC-MS).

In the LC-MS, liquid chromatography (LC) separation was carried out with ACQUITY UPLC (manufactured by Waters Corporation) and mass spectrometry (MS) was carried out with Xevo G2 T of MS (manufactured by Waters Corporation). ACQUITY UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. A sample was prepared in such a manner that [Ir(dmdpq)$_2$(dpm)] was dissolved in toluene at a given concentration and the solution was diluted with acetonitrile. The injection amount was 5.0 μL.

In the MS analysis, ionization was carried out by an electrospray ionization (abbreviation: ESI) method. At this time, the capillary voltage and the sample cone voltage were set to 3.0 kV and 30 V, respectively, and detection was performed in a positive mode. All the components that were ionized under the above conditions were collided with an argon gas in a collision cell to dissociate into product ions. Energy (collision energy) for the collision with argon was 30 eV. A mass range for the measurement was m/z=100-1120. The detection results of the generated product ions by time-of-flight (TOF) MS are shown in FIG. 8.

Figure 8:
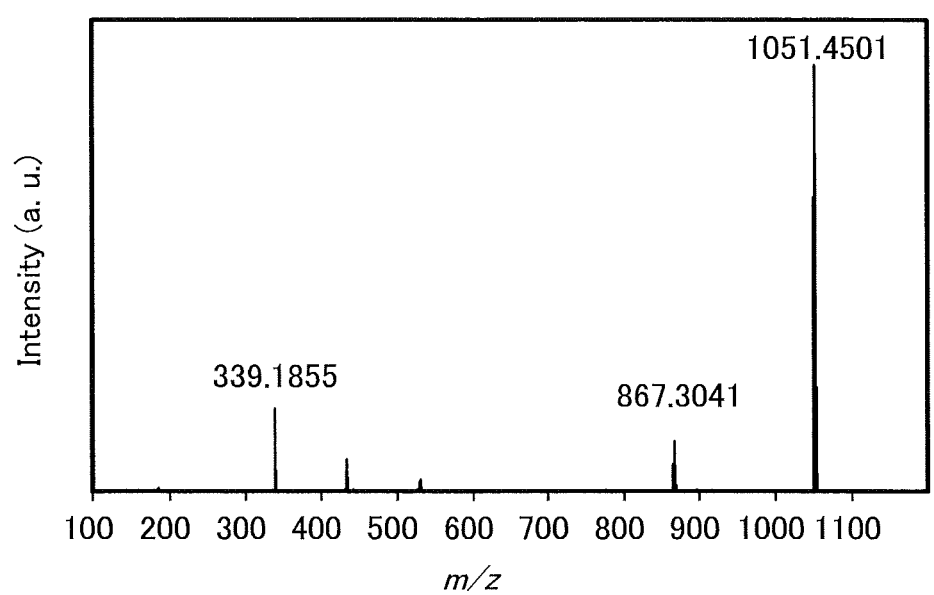
FIG. 8 shows LC-MS measurement results of the organometallic iridium complex represented by Structural Formula (100).

The results in FIG. 8 demonstrate that product ions of [Ir(dmdpq)$_2$(dpm)], which is one embodiment of the present invention and is represented by Structural Formula (100), were detected mainly around m/z=867 and around m/z=339. The results in FIG. 8 are characteristically derived from [Ir(dmdpq)$_2$(dpm)] and can thus be regarded as important data in identification of [Ir(dmdpq)$_2$(dpm)] contained in a mixture.

It is presumed that the product ion around m/z=867 is a cation in a state where dipivaloylmethane and a proton were eliminated from the compound represented by Structural Formula (100), and this is a characteristic of the organometallic iridium complex of one embodiment of the present invention. In addition, it is presumed that the product ion around m/z=339 is a cation in a state where a proton was added to the quinoxaline derivative Hdmdpq, and this indicates a structure of [Ir(dmdpq)$_2$(dpm)] that is the organometallic iridium complex of one embodiment of the present invention.

Furthermore, in this embodiment, it was examined whether the emission wavelength (peak wavelength) of an organometallic iridium complex that has a structure in which a phenyl group that is bonded to a quinoxaline skeleton and bonded to iridium has two substituents that are any of an alkyl group having 1 to 6 carbon atoms, a phenyl group, and a phenyl group having an alkyl group having 1 to 6 carbon atoms as a substituent and the two substituents are bonded to the 4-position and the 6-position of the phenyl group bonded to iridium is longer than the emission wavelength of an organometallic iridium complex that does not have such substituents.

Specifically, emission spectra of the following two organometallic iridium complexes were measured: the organometallic iridium complex [Ir(dmdpq)$_2$(dpm)] described in this example, that is, the organometallic iridium complex having a structure in which a phenyl group that is bonded to a quinoxaline skeleton and bonded to iridium has two substituents (methyl groups) at the 4-position and the 6-position, and an organometallic iridium complex [Ir(dpq)$_2$(acac)], that is, an organometallic iridium complex having a structure in which a phenyl group that is bonded to a quinoxaline skeleton and bonded to iridium does not have such substituents. Structural formulae of the two measured organometallic iridium complexes are shown below.

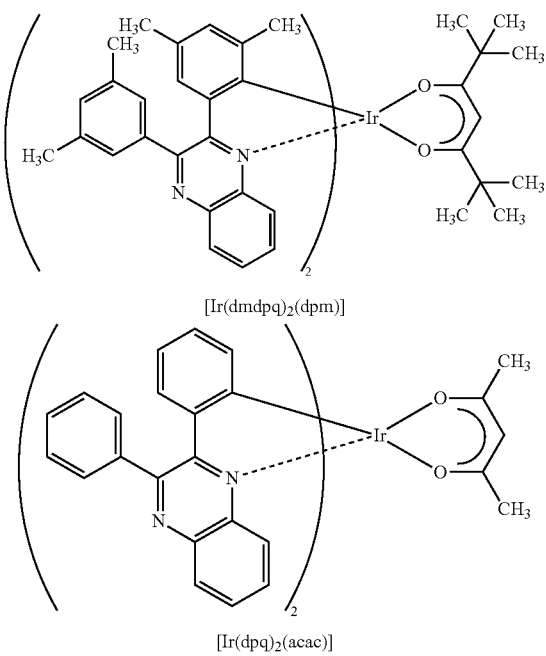

[Ir(dmdpq)$_2$(dpm)]

[Ir(dpq)$_2$(acac)]

Figure 12:
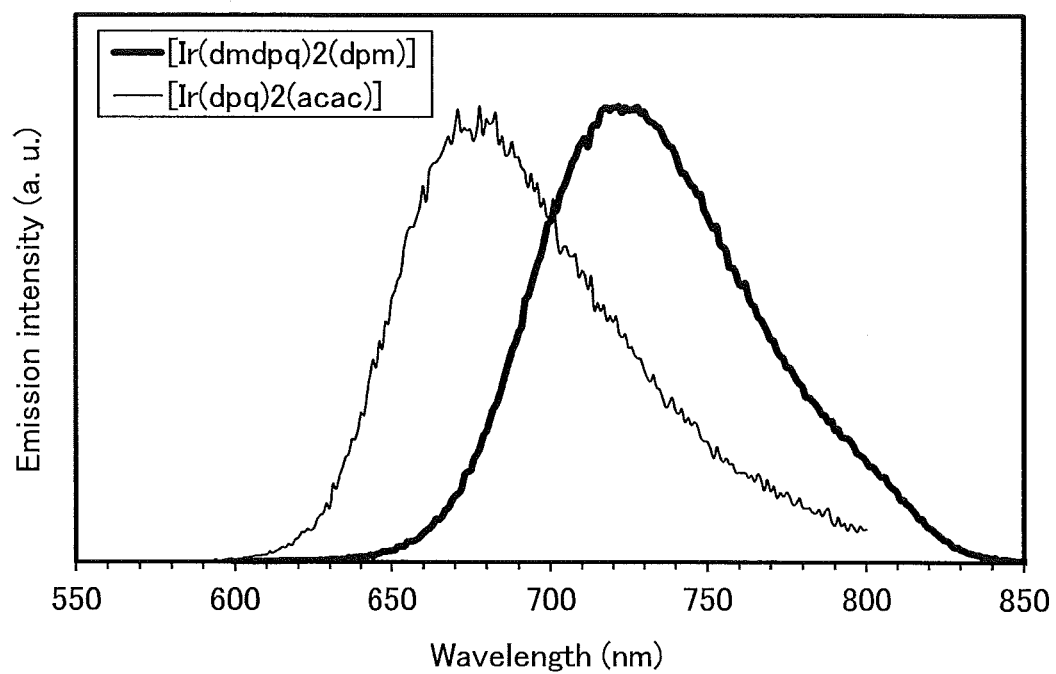
FIG. 12 shows results of comparison between emission spectra of organometallic iridium complexes.

The emission spectra were measured by the above-described method. FIG. 12 shows the measurement results. The measurement results confirm that the emission wavelength of [Ir(dmdpq)$_2$(dpm)] that is one embodiment of the present invention is longer by approximately 50 nm than the emission wavelength of [Ir(dpq)$_2$(acac)] that has the structure in which the phenyl group that is bonded to the quinoxaline skeleton and bonded to iridium does not have the substituents.

Therefore, the results demonstrate that [Ir(dmdpq)$_2$(dpm)] that is one embodiment of the present invention is a novel organometallic iridium complex that emits near-infrared light (emission wavelength: around 700 nm).

Example 2

Synthesis Example 2

In this example, a method of synthesizing bis[4,6-dimethyl-2-(3-methyl-2-quinoxalinyl-κN)phenyl-κC](2,4-pentanedionato-κ$^2$O,O')iridium(III) (abbreviation: [Ir(mdmpq)$_2$(acac)]) that is an organometallic iridium complex of one embodiment of the present invention and is represented by Structural Formula (114) in Embodiment 1 is described. A structure of [Ir(mdmpq)$_2$(acac)] is shown below.

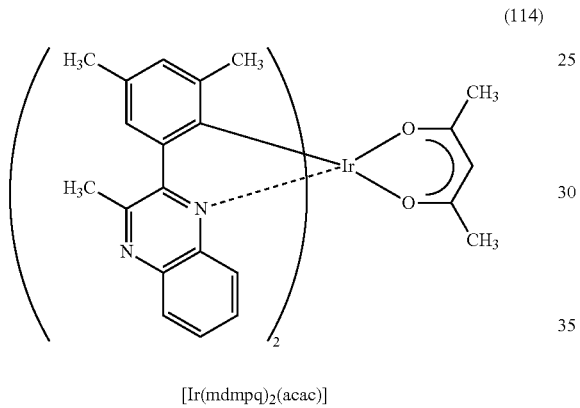

[Ir(mdmpq)$_2$(acac)]

Step 1: Synthesis of 2-(3,5-dimethylphenyl)-3-methylquinoxaline (abbreviation: Hmdmpq)

First, 3.02 g of 2-chloro-3-methylquinoxaline, 3.88 g of 3,5-dimethylphenyl boronic acid, 2.77 g of sodium carbonate, 0.14 g of bis(triphenylphosphine)palladium(II)dichloride (abbreviation: Pd(PPh$_3$)$_2$Cl$_2$), 20 mL of water, and 20 mL of DMF were put in a recovery flask equipped with a reflux pipe, and the air in the flask was replaced with argon. Heating was performed by irradiation with microwaves (2.45 GHz, 100 W) for 2 hours. Then, water was added to this solution, and the organic layer was extracted with dichloromethane. The obtained organic layer was washed with water and saturated saline, and was dried with magnesium sulfate. The solution obtained by the drying was filtered. The solvent of this solution was distilled off, and the obtained residue was purified by flash column chromatography using hexane and ethyl acetate in a volume ratio of 5:1 as a developing solvent. The solid obtained by concentration of a fraction was purified by flash column chromatography using dichloromethane as a developing solvent to give a target quinoxaline derivative, Hmdmpq, as flesh color powder in a yield of 72%. Note that the irradiation with microwaves was performed using a microwave synthesis system (Discover, manufactured by CEM Corporation). Synthesis Scheme (b-1) of Step 1 is shown below.

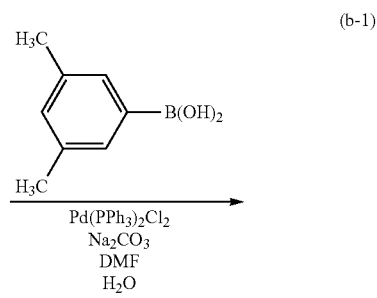

(b-1)

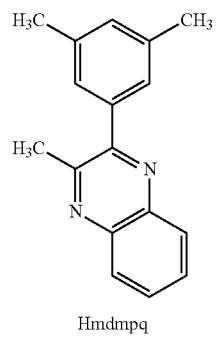

Hmdmpq

Step 2: Synthesis of di-μ-chloro-tetrakis[4,6-dimethyl-2-(3-methyl-2-quinoxalinyl-κN)phenyl-κC]diiridium(III) (abbreviation: [Ir(mdmpq)$_2$Cl]$_2$)

Next, 15 mL of 2-ethoxyethanol, 5 mL of water, 1.00 g of Hmdmpq obtained in Step 1, and 0.57 g of iridium chloride hydrate (IrCl$_3$.H$_2$O) (produced by Sigma-Aldrich Corporation) were put in a recovery flask equipped with a reflux pipe, and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex, [Ir(mdmpq)$_2$Cl]$_2$, as brown powder in a yield of 62%. Synthesis Scheme (b-2) of Step 2 is shown below.

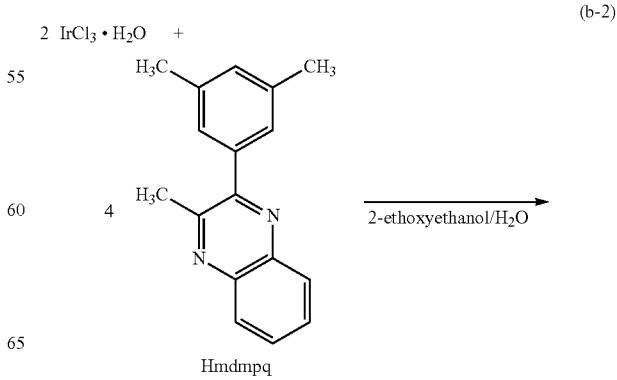

(b-2)

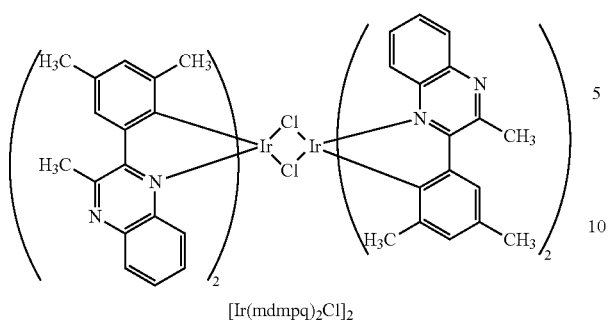

[Ir(mdmpq)₂Cl]₂

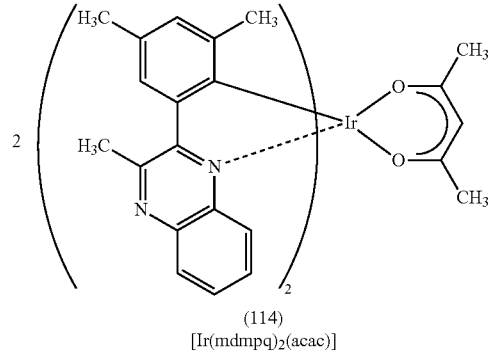

(114)
[Ir(mdmpq)₂(acac)]

Step 3: Synthesis of bis[4,6-dimethyl-2-(3-methyl-2-quinoxalinyl-κN)phenyl-κC](2,4-pentanedionato-κ²O,O')iridium(III) (abbreviation: [Ir(mdmpq)₂(acac)])

Furthermore, 30 mL of 2-ethoxyethanol, 0.86 g of the dinuclear complex, [Ir(mdmpq)₂Cl]₂, obtained in Step 2, 0.18 g of acetylacetone (abbreviation: Hacac), and 0.64 g of sodium carbonate were put in a recovery flask equipped with a reflux pipe, and the air in the flask was replaced with argon. After that, the flask was subjected to irradiation with microwaves (2.45 GHz, 120 W) for 60 minutes to be heated. Here, 0.18 g of Hacac was further added, and heating was performed by irradiation with microwaves (2.45 GHz, 120 W) for 60 minutes. Water was added to the reacted solution and the organic layer was extracted with dichloromethane. The obtained organic layer was washed with water and saturated saline, and was dried with magnesium sulfate. The solution obtained by the drying was filtered. The solvent of this solution was distilled off, and the obtained residue was purified by flash column chromatography using hexane and ethyl acetate in a volume ratio of 5:1 as a developing solvent to give [Ir(mdmpq)₂(acac)], which is the organometallic iridium complex of one embodiment of the present invention, as black powder in a yield of 9%. Synthesis Scheme (b-3) of Step 3 is shown below.

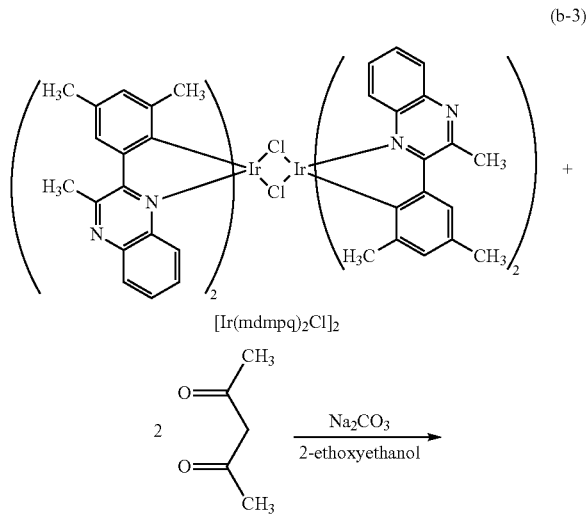

(b-3)

Figure 9:
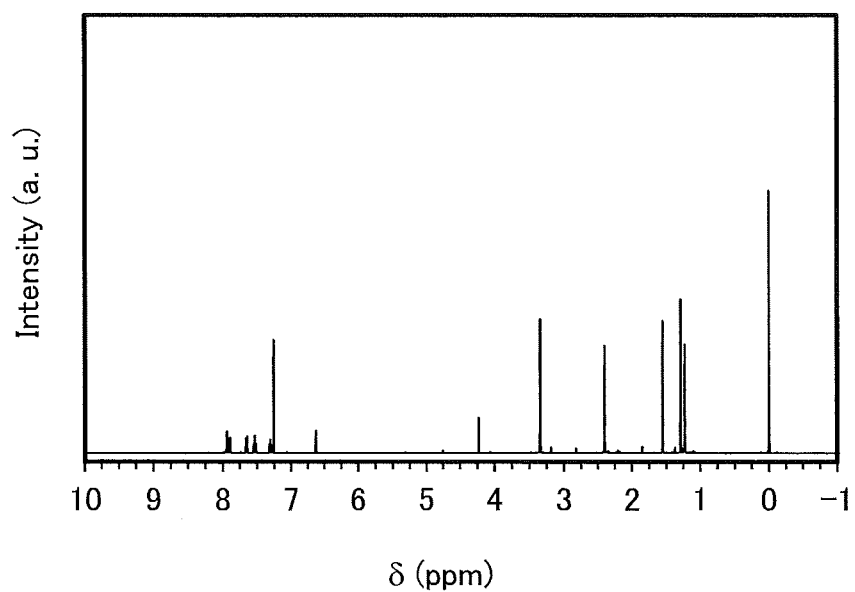
FIG. 9 is a $^1$H-NMR chart of an organometallic iridium complex represented by Structural Formula (114).

Results of analysis of the black powder obtained by the above-described synthesis method by nuclear magnetic resonance spectrometry (¹H-NMR) are shown below. FIG. 9 is the ¹H-NMR chart. The results demonstrate that [Ir(mdmpq)₂(acac)], which is the organometallic iridium complex of one embodiment of the present invention and is represented by Structural Formula (114), was obtained in Synthesis Example 2.

¹H-NMR. δ (CDCl₃): 1.23 (s, 6H), 1.29 (s, 6H), 2.40 (s, 6H), 3.34 (s, 6H), 4.23 (s, 1H), 6.63 (s, 2H), 7.33 (t, 2H), 7.53 (t, 2H), 7.65 (d, 2H), 7.90 (d, 2H), 7.94 (s, 2H).

Figure 10:
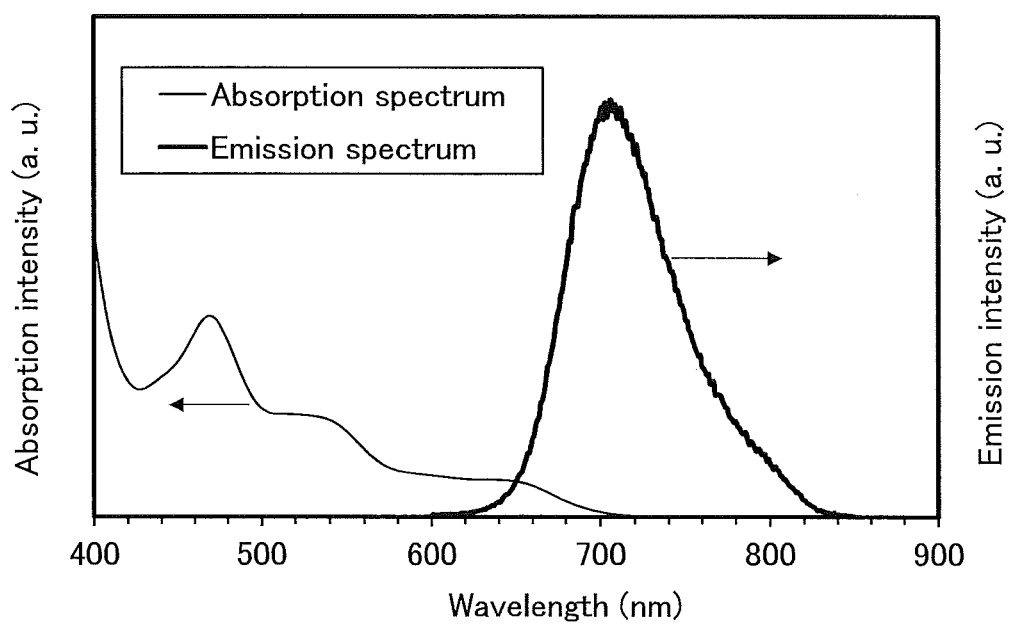
FIG. 10 shows an ultraviolet-visible absorption spectrum and an emission spectrum of the organometallic iridium complex represented by Structural Formula (114).

Next, an ultraviolet-visible absorption spectrum (hereinafter, simply referred to as an absorption spectrum) and an emission spectrum of [Ir(mdmpq)₂(acac)] in a dichloromethane solution were measured. The absorption spectrum was measured with an ultraviolet-visible light spectrophotometer (V550 type, produced by JASCO Corporation) at room temperature in the state where the dichloromethane solution (0.089 mmol/L) was in a quartz cell. In addition, the measurement of the emission spectrum was conducted at room temperature, for which a fluorescence spectrophotometer (FS920 manufactured by Hamamatsu Photonics K.K.) was used and the degassed dichloromethane solution (0.089 mmol/L) was put in a quartz cell. FIG. 10 shows measurement results of the absorption spectrum and emission spectrum. The horizontal axis represents wavelength and the vertical axes represent absorption intensity and emission intensity. In FIG. 10, two solid lines are shown: a thin line represents the absorption spectrum, and a thick line represents the emission spectrum. The absorption spectrum shown in FIG. 10 was obtained by subtraction of the absorption spectra of the dichloromethane and the quartz from the obtained absorption spectrum.

As shown in FIG. 10, [Ir(mdmpq)₂(acac)] that is the organometallic iridium complex of one embodiment of the present invention has an absorption peak at 470 nm and an emission peak at 706 nm. In addition, deep red light emission was observed in the dichloromethane solution.

Next, [Ir(mdmpq)₂(acac)] obtained in this example was subjected to a MS analysis by liquid chromatography mass spectrometry (LC-MS).

In the LC-MS, liquid chromatography (LC) separation was carried out with ACQUITY UPLC (manufactured by Waters Corporation) and mass spectrometry (MS) was carried out with Xevo G2 T of MS (manufactured by Waters Corporation). ACQUITY UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. A sample was prepared in such a manner that [Ir(mdmpq)$_2$(acac)] was dissolved in toluene at a given concentration and the solution was diluted with acetonitrile. The injection amount was 5.0 μL.

In the MS analysis, ionization was carried out by an electrospray ionization (abbreviation: ESI) method. At this time, the capillary voltage and the sample cone voltage were set to 3.0 kV and 30 V, respectively, and detection was performed in a positive mode. All the components that were ionized under the above conditions were collided with an argon gas in a collision cell to dissociate into product ions. Energy (collision energy) for the collision with argon was 50 eV. A mass range for the measurement was m/z=100-1200. The detection results of the generated product ions by time-of-flight (TOF) MS are shown in FIG. 11.

Figure 11:
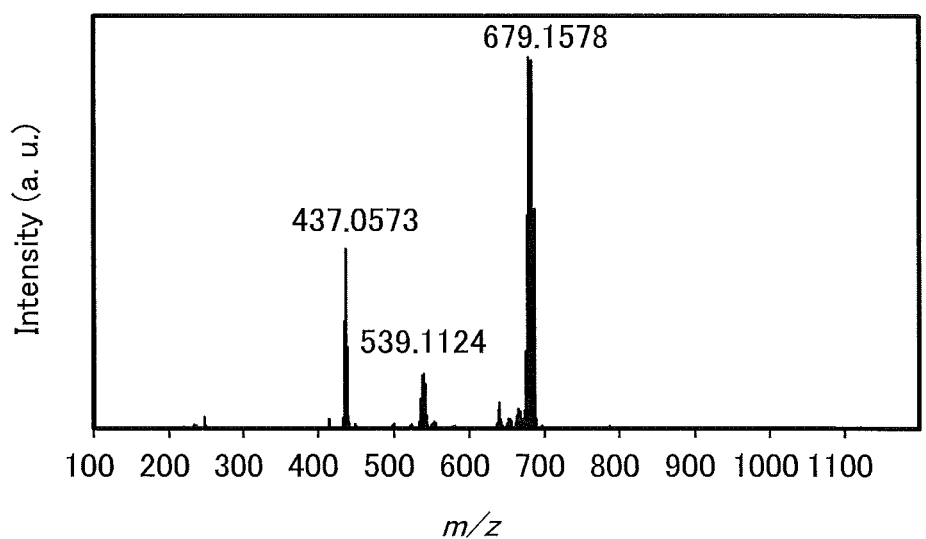
FIG. 11 shows LC-MS measurement results of the organometallic iridium complex represented by Structural Formula (114).

The results in FIG. 11 demonstrate that product ions of [Ir(mdmpq)$_2$(acac)], which is one embodiment of the present invention and is represented by Structural Formula (114), were detected mainly around m/z=679, around m/z=539, and around m/z=437. The results in FIG. 11 are characteristically derived from [Ir(mdmpq)$_2$(acac)] and can thus be regarded as important data in identification of [Ir(mdmpq)$_2$(acac)] contained in a mixture.

It is presumed that the product ion around m/z=679 is a cation in a state where acetylacetone and a proton were eliminated from the compound represented by Structural Formula (114), and this is a characteristic of the organometallic iridium complex of one embodiment of the present invention. In addition, it is presumed that the product ion around m/z=539 is a cation in a state where the quinoxaline derivative Hmdmpq was eliminated from the compound represented by Structural Formula (114) and that the product ion around m/z=437 is a cation in a state where acetylacetone and a proton were eliminated from the product ion around=m/z 539, which indicates a structure of [Ir(mdmpq)$_2$(acac)] that is the organometallic iridium complex of one embodiment of the present invention.

Furthermore, in this embodiment, it was examined whether the emission wavelength (peak wavelength) of an organometallic iridium complex that has a structure in which a phenyl group that is bonded to a quinoxaline skeleton and bonded to iridium has two substituents that are any of an alkyl group having 1 to 6 carbon atoms, a phenyl group, and a phenyl group having an alkyl group having 1 to 6 carbon atoms as a substituent and the two substituents are bonded to the 4-position and the 6-position of the phenyl group bonded to iridium is longer than the emission wavelength of an organometallic iridium complex that does not have such substituents.

Specifically, emission spectra of the following two organometallic iridium complexes were measured: the organometallic iridium complex [Ir(mdmpq)$_2$(acac)] described in this example, that is the organometallic iridium complex having a structure in which a phenyl group that is bonded to a quinoxaline skeleton and bonded to iridium has two substituents (methyl groups) at the 4-position and the 6-position, and an organometallic iridium complex [Ir(mpq)$_2$(acac)], that is, an organometallic iridium complex having a structure in which a phenyl group that is bonded to a quinoxaline skeleton and bonded to iridium does not have such substituents. Structural formulae of the two measured organometallic iridium complexes are shown below.

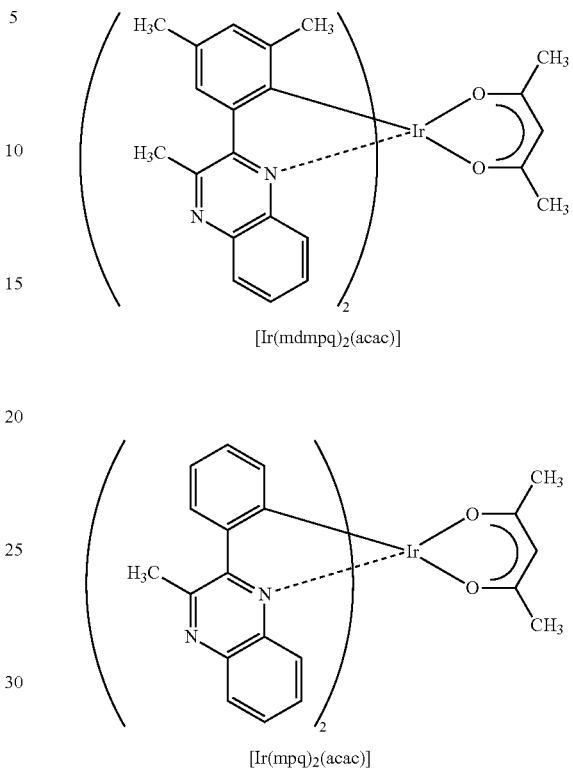

[Ir(mdmpq)$_2$(acac)]

[Ir(mpq)$_2$(acac)]

Figure 13:
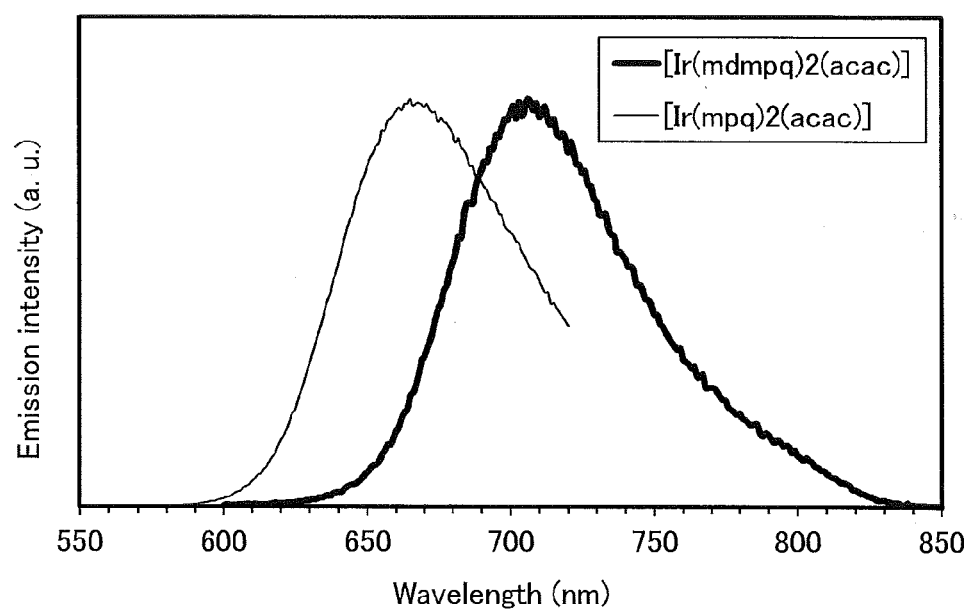
FIG. 13 shows results of comparison between emission spectra of organometallic iridium complexes.

The emission spectra were measured by the above-described method. FIG. 13 shows the measurement results. The measurement results confirm that the emission wavelength of [Ir(mdmpq)$_2$(acac)] that is one embodiment of the present invention is longer by approximately 50 nm than the emission wavelength of [Ir(mpq)$_2$(acac)] that has the structure in which the phenyl group that is bonded to the quinoxaline skeleton and bonded to iridium does not have the substituents.

Therefore, the results demonstrate that [Ir(mdmpq)$_2$(acac)] that is one embodiment of the present invention is a novel organometallic iridium complex that emits near-infrared light (emission wavelength: around 700 nm).

Example 3

Synthesis Example 3

In this example, a method of synthesizing bis[4,6-bis(2-methylpropyl)-2-(3-methyl-2-quinoxalinyl-κN)phenyl-κC] (2,4-pentanedionato-κ$^2$O,O')iridium(III) (abbreviation: [Ir(mdiBupq)$_2$(acac)]) that is an organometallic iridium complex of one embodiment of the present invention and is represented by Structural Formula (118) in Embodiment 1 is described. A structure of [Ir(mdiBupq)$_2$(acac)] is shown below.

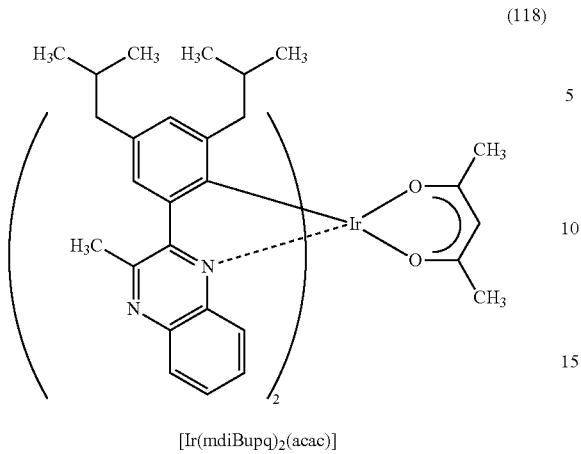

[Ir(mdiBupq)₂(acac)]

Step 1: Synthesis of 2-(3,5-dichlorophenyl)-3-methylquinoxaline

First, 1.00 g of 2-chloro-3-methylquinoxaline, 0.84 g of 3,5-dichlorophenyl boronic acid, 1.68 g of potassium carbonate, 0.049 g of tri(o-tolyl)phosphine, 20 mL of toluene, 5 mL of ethanol, and 6 mL of water were put in a three-neck flask equipped with a reflux pipe, and the air in the flask was replaced with nitrogen. The inside of the flask was degassed under reduced pressure, 0.018 g of palladium acetate was added thereto, and the mixture was heated at 80° C. for 19 hours. Then, water was added to this solution, and the organic layer was extracted with toluene. The obtained organic layer was washed with water and saturated saline, and was dried with magnesium sulfate. The solution obtained by the drying was filtered. The solvent of this solution was distilled off, and then the obtained residue was purified by flash column chromatography using hexane and ethyl acetate in a volume ratio of 5:1 as a developing solvent to give a target quinoxaline derivative as pale pink powder in a yield of 67%). Synthesis Scheme (c-1) of Step 1 is shown below.

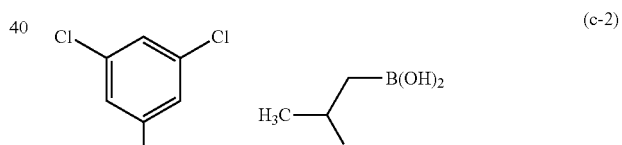

Step 2: Synthesis of 2-[3,5-bis(2-methylpropyl)phenyl]-3-methylquinoxaline (abbreviation: HmdiBupq)

Next, 0.76 g of 2-(3,5-dichlorophenyl)-3-methylquinoxaline obtained in Step 1, 1.00 g of (2-methylpropyl)boronic acid, 2.09 g of tripotassium phosphate, 0.041 g of 2-dicyclohexylphosphino-2',6'-dimethoxybiphenyl (abbreviation: S-Phos), and 45 mL of toluene were put in a three-neck flask equipped with a reflux pipe, and the air in the flask was replaced with nitrogen. The inside of the flask was degassed under reduced pressure, 0.024 g of tris(dibenzylideneacetone)dipalladium(0) was added thereto, and the mixture was refluxed for 6.5 hours. Then, water was added to this solution, and the organic layer was extracted with toluene. The obtained organic layer was washed with water and saturated saline, and was dried with magnesium sulfate. The solution obtained by the drying was filtered. This solution was filtered through a filter aid in which Celite, alumina, and Celite were stacked in this order and the toluene solvent was distilled off to give a target quinoxaline derivative HmdiBupq as orange oil in a yield of 82%. Synthesis Scheme (c-2) of Step 2 is shown below.

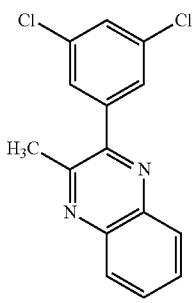

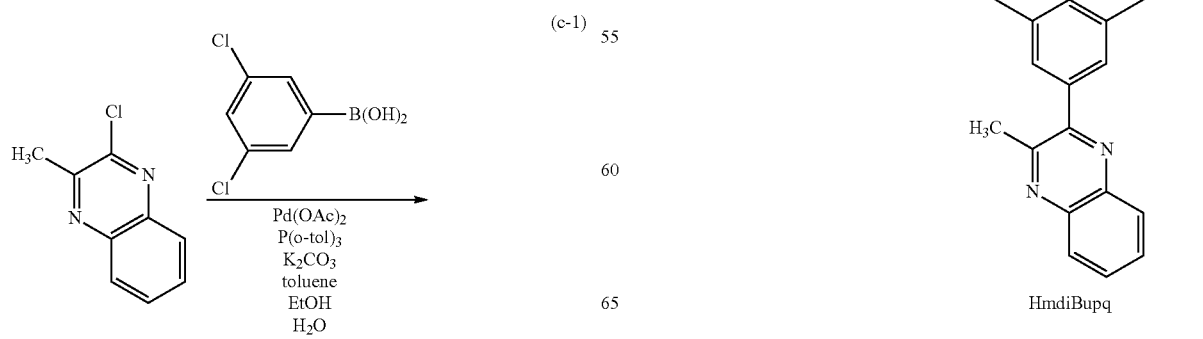

Step 3: Synthesis of di-μ-chloro-tetrakis[4,6-bis(2-methylpropyl)-2-(3-methyl-2-quinoxalinyl-κN)phenyl-κC]diiridium(III) (abbreviation: [Ir(mdiBupq)$_2$Cl]$_2$)

Next, 15 mL of 2-ethoxyethanol, 5 mL of water, 1.75 g of HmdiBupq obtained in Step 2, and 0.80 g of iridium chloride hydrate (IrCl$_3$·H$_2$O) (produced by Sigma-Aldrich Corporation) were put in a recovery flask equipped with a reflux pipe, and the air in the flask was replaced with argon. After that, irradiation with microwaves (2.45 GHz, 100 W) was performed for 1 hour to cause a reaction. The solvent was distilled off, and then the obtained residue was suction-filtered and washed with hexane to give a dinuclear complex [Ir(mdiBupq)$_2$Cl]$_2$ as brown powder in a yield of 71%. Synthetic Scheme (c-3) of Step 3 is shown below.

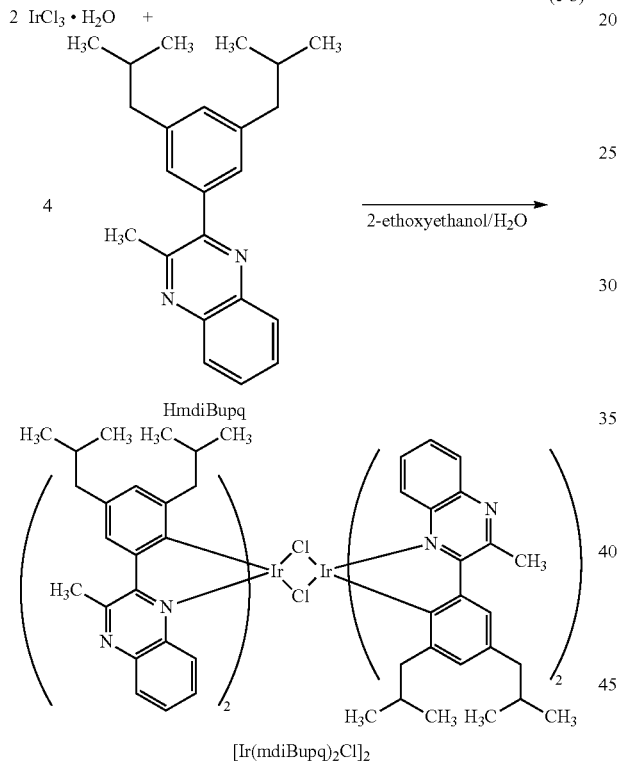

Step 4: Synthesis of bis[4,6-bis(2-methylpropyl)-2-(3-methyl-2-quinoxalinyl-κN)phenyl-κC](2,4-pentadionato-κ$^2$O,O')iridium(III) (abbreviation: [Ir(mdiBupq)$_2$(acac)])

Furthermore, 30 mL of 2-ethoxyethanol, 2.32 g of the dinuclear complex [Ir(mdiBupq)$_2$Cl]$_2$ obtained in Step 3, 0.39 g of acetylacetone (abbreviation: Hacac), and 1.41 g of sodium carbonate were put in a recovery flask equipped with a reflux pipe, and the air in the flask was replaced with argon. After that, the flask was subjected to irradiation with microwaves (2.45 GHz, 120 W) for 60 minutes to be heated. Here, 0.39 g of Hacac was further added, and heating was performed by irradiation with microwaves (2.45 GHz, 200 W) for 60 minutes. Water was added to this solution, and the organic layer was extracted with dichloromethane. The obtained organic layer was washed with water and saturated saline, and was dried with magnesium sulfate. The solution obtained by the drying was filtered. The solvent of this solution was distilled off. The obtained residue was purified by flash column chromatography using dichloromethane as a developing solvent and recrystallized with a mixed solvent of dichloromethane and methanol to give [ft(mdiBupq)$_2$(acac)], which is the organometallic iridium complex of one embodiment of the present invention, as black powder in a yield of 4%. Synthesis Scheme (c-4) of Step 4 is shown below.

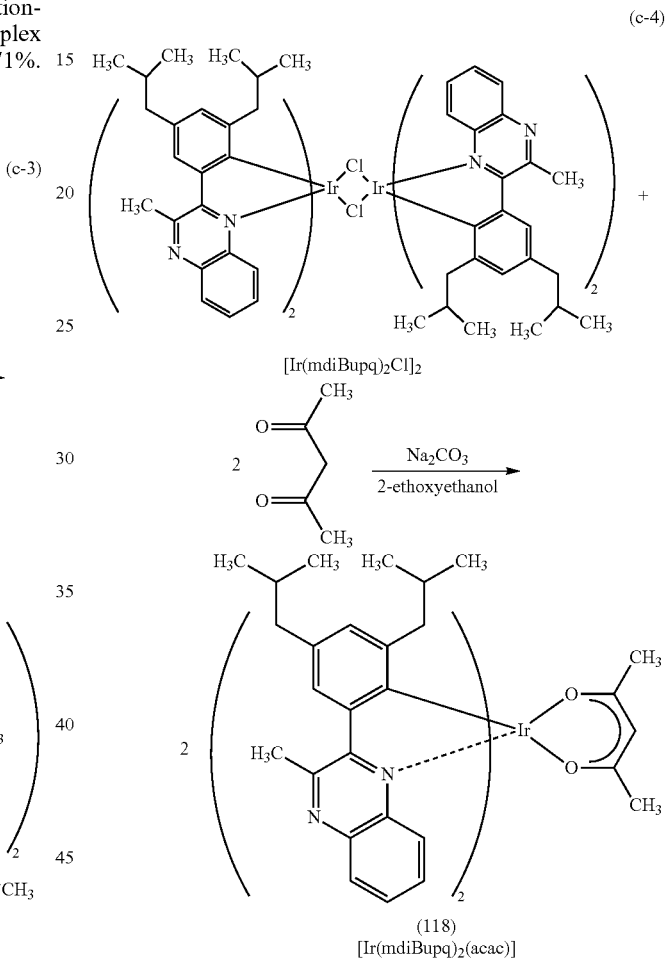

Figure 14:
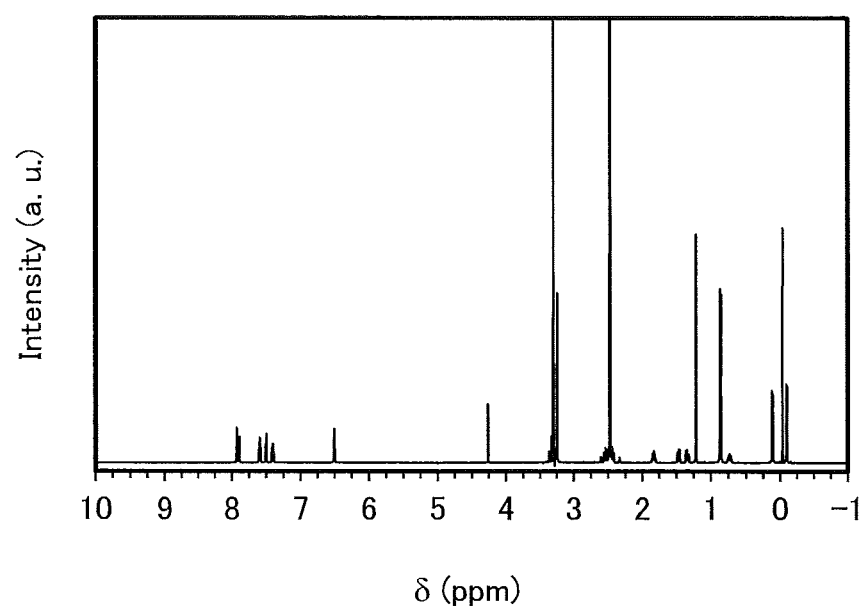
FIG. 14 is a $^1$H-NMR chart of an organometallic iridium complex represented by Structural Formula (118).

Results of analysis of the black powder obtained by the above-described synthesis method by nuclear magnetic resonance spectrometry ($^1$H-NMR) are shown below. FIG. 14 is the $^1$H-NMR chart. The results demonstrate that [Ir(mdiBupq)$_2$(acac)], which is the organometallic iridium complex of one embodiment of the present invention and is represented by Structural Formula (118), was obtained in Synthesis Example 3.

$^1$H-NMR. δ (CDCl$_3$): −0.06 (d, 6H), 0.15 (d, 6H), 0.74-0.79 (m, 2H), 0.89 (d, 12H), 1.25 (s, 6H), 1.35-1.39 (m, 2H), 1.48-1.52 (m, 2H), 1.83-1.89 (m, 2H), 2.44-2.48 (m, 2H), 2.55-2.60 (m, 2H), 3.28 (s, 6H), 4.29 (s, 1H), 6.54 (s, 2H), 7.44 (t, 2H), 7.53 (d, 2H), 7.63 (t, 2H), 7.93 (d, 2H), 7.96 (s, 2H).

Figure 15:
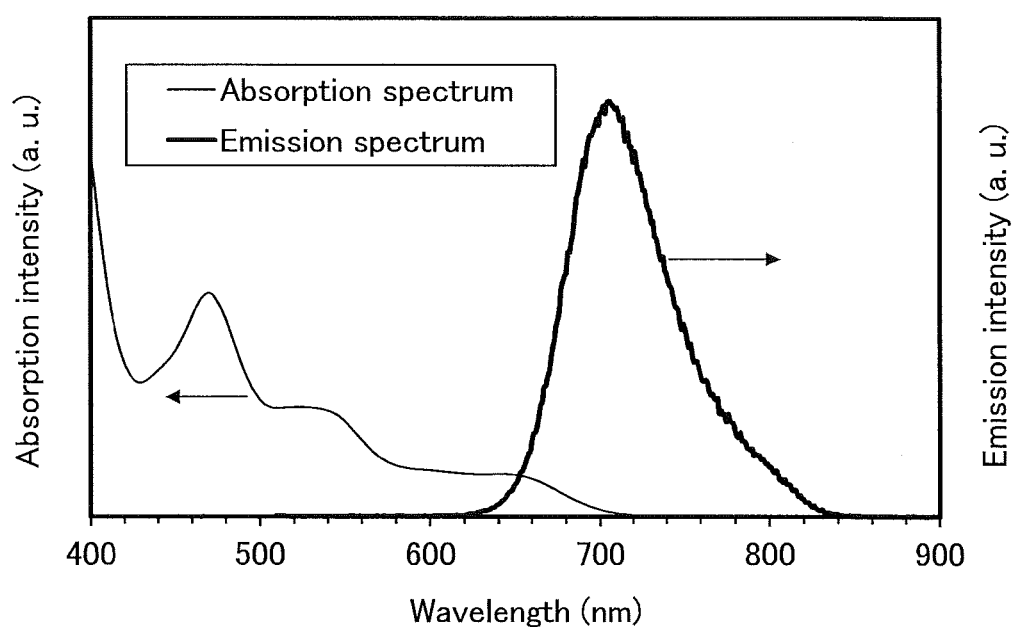
FIG. 15 shows an ultraviolet-visible absorption spectrum and an emission spectrum of the organometallic iridium complex represented by Structural Formula (118).

Next, an ultraviolet-visible absorption spectrum (hereinafter, simply referred to as an absorption spectrum) and an emission spectrum of [Ir(mdiBupq)$_2$(acac)] in a dichloromethane solution were measured. The absorption spectrum was measured with an ultraviolet-visible light spectrophotometer (V550 type, produced by JASCO Corporation) at room temperature in the state where the dichloromethane solution (0.070 mmol/L) was in a quartz cell. In addition, the measurement of the emission spectrum was conducted at room temperature, for which a fluorescence spectrophotometer (FS920 manufactured by Hamamatsu Photonics K.K.) was used and the degassed dichloromethane solution (0.070 mmol/L) was put in a quartz cell. FIG. 15 shows measurement results of the absorption spectrum and emission spectrum. The horizontal axis represents wavelength and the vertical axes represent absorption intensity and emission intensity. In FIG. 15, two solid lines are shown: a thin line represents the absorption spectrum, and a thick line represents the emission spectrum. The absorption spectrum shown in FIG. 15 was obtained by subtraction of the absorption spectra of the dichloromethane and the quartz from the obtained absorption spectrum.

As shown in FIG. 15, [ft(mdiBupq)$_2$(acac)] that is the organometallic iridium complex of one embodiment of the present invention has an absorption peak at 473 nm and an emission peak at 706 nm. In addition, deep red light emission was observed in the dichloromethane solution.

Furthermore, in this embodiment, it was examined whether the emission wavelength (peak wavelength) of an organometallic iridium complex that has a structure in which a phenyl group that is bonded to a quinoxaline skeleton and bonded to iridium has two substituents that are any of an alkyl group having 1 to 6 carbon atoms, a phenyl group, and a phenyl group having an alkyl group having 1 to 6 carbon atoms as a substituent and the two substituents are bonded to the 4-position and the 6-position of the phenyl group bonded to iridium is longer than the emission wavelength of an organometallic iridium complex that does not have such substituents.

Specifically, emission spectra of the following two organometallic iridium complexes were measured: the organometallic iridium complex [Ir(mdiBupq)$_2$(acac)] described in this example, that is the organometallic iridium complex having a structure in which a phenyl group that is bonded to a quinoxaline skeleton and bonded to iridium has two substituents (methyl groups) at the 4-position and the 6-position, and an organometallic iridium complex [Ir(mpq)$_2$(acac)], that is, an organometallic iridium complex having a structure in which a phenyl group that is bonded to a quinoxaline skeleton and bonded to iridium does not have such substituents. Structural formulae of the two measured organometallic iridium complexes are shown below.

[Ir(mdiBupq)$_2$(acac)]

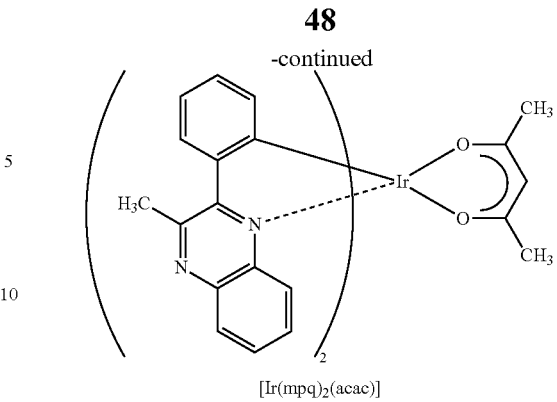

[Ir(mpq)$_2$(acac)]

Figure 16:
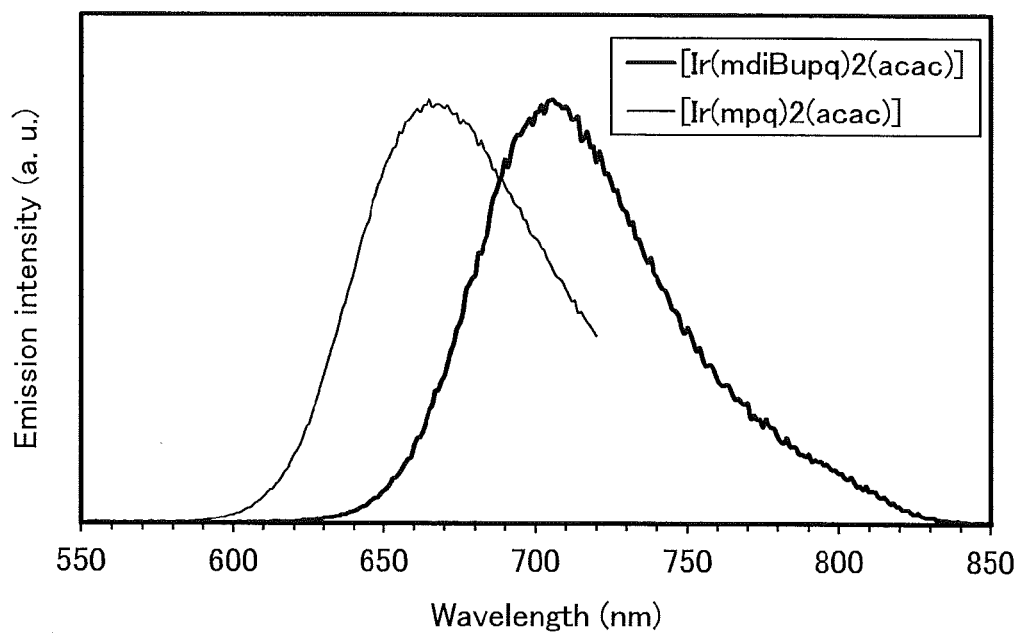
FIG. 16 shows results of comparison between emission spectra of organometallic iridium complexes.

The emission spectra were measured by the above-described method. FIG. 16 shows the measurement results. The measurement results confirm that the emission wavelength of [Ir(mdiBupq)$_2$(acac)] that is one embodiment of the present invention is longer by approximately 50 nm than the emission wavelength of [Ir(mpq)$_2$(acac)] that has the structure in which the phenyl group that is bonded to the quinoxaline skeleton and bonded to iridium does not have the substituents.

Therefore, the results demonstrate that [Ir(mdiBupq)$_2$(acac)] that is one embodiment of the present invention is a novel organometallic iridium complex that emits near-infrared light (emission wavelength: around 700 nm).

Example 4

Figure 17:
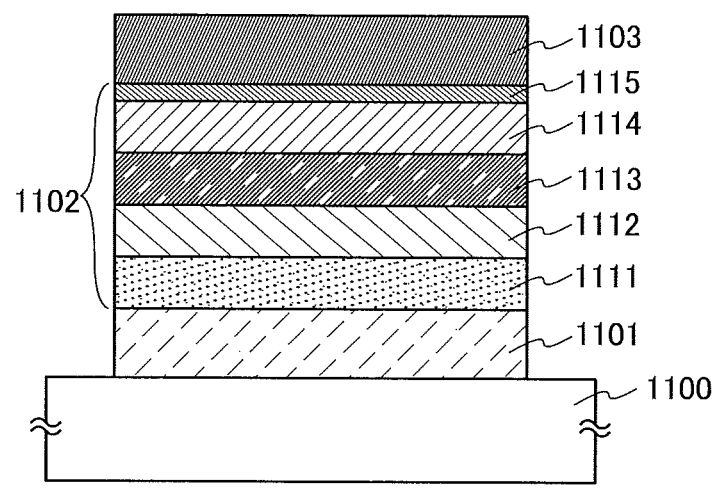
FIG. 17 illustrates a light-emitting element.

In this example, a light-emitting element 1 in which [Ir(dmdpq)$_2$(dpm)] (Structural Formula (100)) that is the organometallic iridium complex of one embodiment of the present invention was used in a light-emitting layer, a light-emitting element 2 in which [Ir(mdmpq)$_2$(acac)] (Structural Formula (114)) that is the organometallic iridium complex of one embodiment of the present invention was used in a light-emitting layer, and a light-emitting element 3 in which [Ir(mdiBupq)$_2$(acac)] (Structural Formula (118)) that is the organometallic iridium complex of one embodiment of the present invention was used in a light-emitting layer were fabricated, and emission spectra of the light-emitting elements were measured. Note that the fabrication of each of the light-emitting element 1, the light-emitting element 2, and the light-emitting element 3 is described with reference to FIG. 17. Chemical formulae of materials used in this example are shown below.

DBT3P-II

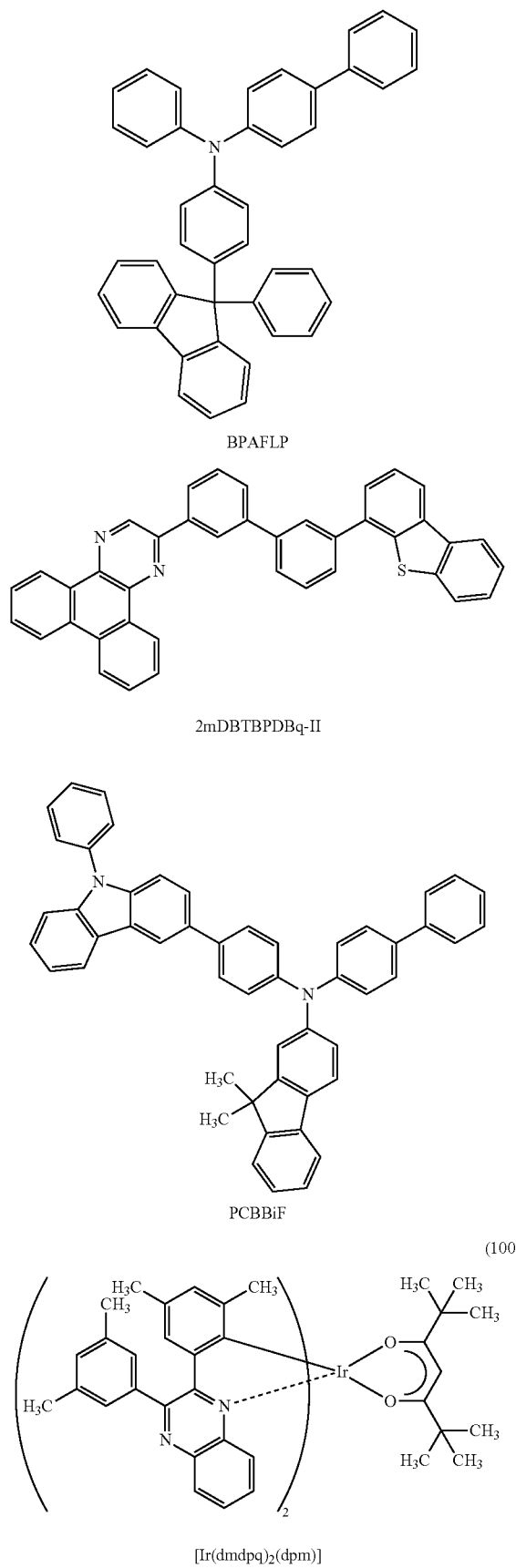

BPAFLP

2mDBTBPDBq-II

PCBBiF

[Ir(dmdpq)$_2$(dpm)] (100)

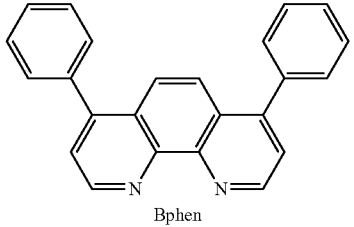

Bphen

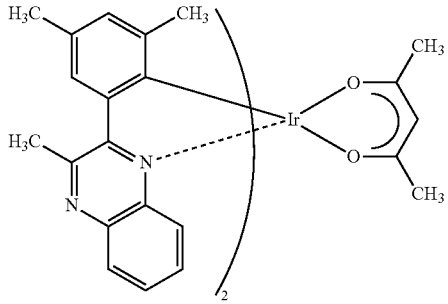

[Ir(mdmpq)$_2$(acac)] (114)

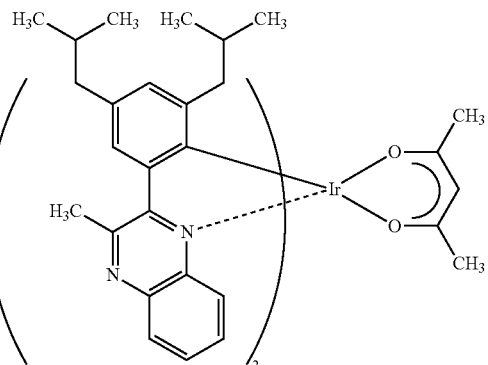

[Ir(mdiBupq)$_2$(acac)] (118)

<<Fabrication of Light-Emitting Element 1, Light-Emitting Element 2, and Light-Emitting Element 3>>

First, indium tin oxide containing silicon oxide (ITSO) was deposited over a glass substrate 1100 by a sputtering method, so that a first electrode 1101 functioning as an anode was formed. The thickness of the first electrode 1101 was 110 nm. The electrode area was 2 mm×2 mm.

Next, as pretreatment for forming each of the light-emitting elements 1 to 3 over the substrate 1100, the surface of the substrate was washed, baked at 200° C. for 1 hour, and subjected to UV ozone treatment for 370 seconds After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case is described in which a hole-injection layer 1111, a hole-transport layer 1112, a light-emitting layer 1113, an electron-transport layer 1114, and an electron-injection layer 1115, which are included in an EL layer 1102, are sequentially formed by a vacuum evaporation method.

After reducing the pressure in the vacuum evaporation apparatus to $10^{-4}$ Pa, 1,3,5-tri(dibenzothiophen-4-yl)benzene (abbreviation: DBT3P-II) and molybdenum(VI) oxide were deposited by co-evaporation so that the mass ratio of DBT3P-II (abbreviation) to molybdenum oxide was 4:2, whereby the hole-injection layer 1111 was formed over the first electrode 1101. The thickness of the hole-injection layer 1111 was 20 nm. Note that the co-evaporation is an evaporation method in which a plurality of different substances are vaporized from the respective evaporation sources at the same time.

Then, 4-phenyl-4'-(9-phenylfluoren-9-yl)triphenylamine (abbreviation: BPAFLP) was deposited by evaporation to a thickness of 20 nm, whereby the hole-transport layer 1112 was formed.

Then, on the light-emitting layer 1113, 2mDBTBPDBq-II was deposited by evaporation to a thickness of 20 nm and then bathophenanthroline (abbreviation: Bphen) was deposited by evaporation to a thickness of 10 nm, whereby the electron-transport layer 1114 was formed. Furthermore, lithium fluoride was deposited by evaporation to a thickness of 1 nm on the electron-transport layer 1114, whereby the electron-injection layer 1115 was formed.

Finally, aluminum was deposited by evaporation to a thickness of 200 nm on the electron-injection layer 1115, whereby the second electrode 1103 serving as a cathode was formed. Through the above-described steps, the light-emitting elements 1 to 3 were fabricated. Note that in all the above evaporation steps, evaporation was performed by a resistance-heating method.

Table 3 shows element structures of the light-emitting elements 1 to 3 fabricated in the above-described manner.

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 1 | ITSO (110 nm) | DBT3P-II:MoOx (4:2 20 nm) | BPAFLP (20 nm) | * | 2mDBTBPDBq-II (20 nm) | Bphen (10 nm) | LiF (1 nm) | Al (200 nm) |
| Light-emitting element 2 | ITSO (110 nm) | DBT3P-II:MoOx (4:2 20 nm) | BPAFLP (20 nm) | ** | 2mDBTBPDBq-II (20 nm) | Bphen (10 nm) | LiF (1 nm) | Al (200 nm) |
| Light-emitting element 3 | ITSO (110 nm) | DBT3P-II:MoOx (4:2 20 nm) | BPAFLP (20 nm) | *** | 2mDBTBPDBq-II (20 nm) | Bphen (10 nm) | LiF (1 nm) | Al (200 nm) |

* 2mDBTBPDBq-II:PCBBiF:[Ir(dmdpq)$_2$(dpm)] (0.8:0.2:0.05 40 nm)
** 2mDBTBPDBq-II:PCBBiF:[Ir(mdmpq)$_2$(acac)] (0.8:0.2:0.05 40 nm)
*** 2mDBTBPDBq-II:PCBBiF:[Ir(mdiBupq)$_2$(acac)] (0.8:0.2:0.05 40 nm)

Next, the light-emitting layer 1113 was formed on the hole-transport layer 1112. In the case of the light-emitting element 1, 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-N-[4-(9-phenyl-9H-carbazol-3-yl)phenyl]-9,9-dimethyl-9H-fluoren-2-amine (abbreviation: PCBBiF), and bis{4,6-dimethyl-2-[3-(3,5-dimethylphenyl)-2-quinoxalinyl-κN]phenyl-κC}(2,2',6,6'-tetramethyl-3,5-heptanedionato-κ$^2$O,O')iridium(III) (abbreviation: [Ir(dmdpq)$_2$(dpm)]) were deposited by co-evaporation so that the weight ratio of 2mDBTBPDBq-II to PCBBiF and [Ir(dmdpq)$_2$(dpm)] was 0.8:0.2:0.05. The thickness of the light-emitting layer 1113 in the light-emitting element 1 was 40 nm.

In the case of the light-emitting element 2, 2mDBTBPDBq-II, PCBBiF, and bis[4,6-dimethyl-2-(3-methyl-2-quinoxalinyl-κN)phenyl-κC](2,4-pentanedionato-κ$^2$O,O')iridium(III) (abbreviation: [Ir(mdmpq)$_2$(acac)]) were deposited by co-evaporation so that the weight ratio of 2mDBTBPDBq-II to PCBBiF and [Ir(mdmpq)$_2$(acac)] was 0.8:0.2:0.05. The thickness of the light-emitting layer 1113 in the light-emitting element 2 was 40 nm.

In the case of the light-emitting element 3, 2mDBTBPDBq-II, PCBBiF, and bis[4,6-bis(2-methylpropyl)-2-(3-methyl-2-quinoxalinyl-κN)phenyl-κC](2,4-pentadionato-κ$^2$O,O')iridium(III) (abbreviation: [Ir(mdiBupq)$_2$(acac)]) were deposited by co-evaporation so that the weight ratio of 2mDBTBPDBq-II to PCBBiF and [Ir(mdiBupq)$_2$(acac)] was 0.8:0.2:0.05. The thickness of the light-emitting layer 1113 in the light-emitting element 3 was 40 nm.

Furthermore, the fabricated light-emitting elements 1 to 3 were sealed in a glove box containing a nitrogen atmosphere so as not to be exposed to the air (specifically, a sealant was applied onto outer edges of the elements, and at the time of sealing, first, UV treatment was performed and then heat treatment was performed at 80° C. for 1 hour).

<<Emission Characteristics of Light-Emitting Element 1, Light-Emitting Element 2, and Light-Emitting Element 3>>

Emission characteristics of the fabricated light-emitting element 1, light-emitting element 2, and light-emitting element 3 were measured.

Figure 18:
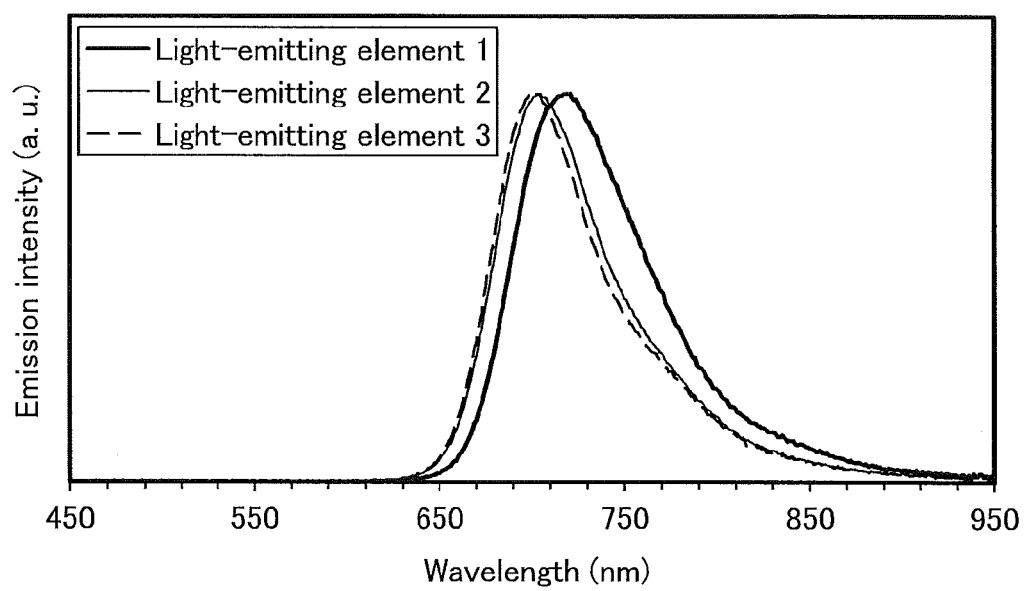
FIG. 18 shows emission spectra of a light-emitting element 1, a light-emitting element 2, and a light-emitting element 3.

FIG. 18 shows emission spectra of the light-emitting elements 1 to 3 that were obtained when current was applied to the light-emitting elements 1 to 3 at a current density of 25 mA/cm$^2$. As shown in FIG. 18, the emission spectrum of the light-emitting element 1 has a peak at around 722 nm, which indicates that the peak is derived from emission of the organometallic iridium complex [Ir(dmdpq)$_2$(dpm)]. The emission spectrum of the light-emitting element 2 has a peak at around 708 nm, which indicates that the peak is derived from emission of the organometallic iridium complex [Ir(mdmpq)$_2$(acac)]. The emission spectrum of the light-emitting element 3 has a peak at around 702 nm, which indicates that the peak is derived from emission of the organometallic iridium complex [Ir(mdiBupq)$_2$(acac)].

Thus, it was confirmed that emission from the organometallic iridium complexes emitting near-infrared light (emission wavelength: 700 nm) was obtained in all of the light-emitting elements. In other words, the use of the organometallic iridium complex of one embodiment of the present invention for a light-emitting element allows the light-emitting element to have high emission efficiency and a long lifetime and emits near-infrared light (emission wavelength: around 700 nm).

Comparative Example

In this comparative example, it was examined whether or not a structure in which a phenyl group that is bonded to a skeleton that is not a quinoxaline skeleton and bonded to iridium has two substituents that are any of an alkyl group having 1 to 6 carbon atoms, a phenyl group, and a phenyl group having an alkyl group having 1 to 6 carbon atoms as a substituent, and the two substituents are bonded to the 4-position and the 6-position of the phenyl group bonded to iridium is effective in making the emission wavelength (peak wavelength) of an organometallic iridium complex having the structure longer than the emission wavelength of an organometallic iridium complex that does not have such substituents.

Specifically, emission spectra of the following two organometallic iridium complexes were measured: an organometallic iridium complex [Ir(tBudmppm)$_2$(acac)], that is an organometallic iridium complex having a structure in which a phenyl group that is bonded to a pyrimidine skeleton and bonded to iridium has two substituents (methyl groups) at the 4-position and the 6-position, and an organometallic iridium complex [Ir(tBuppm)$_2$(acac)], that is an organometallic iridium complex having a structure in which a phenyl group that is bonded to a pyrimidine skeleton and bonded to iridium does not have such substituents. Structural formulae of the two measured organometallic iridium complexes are shown below.

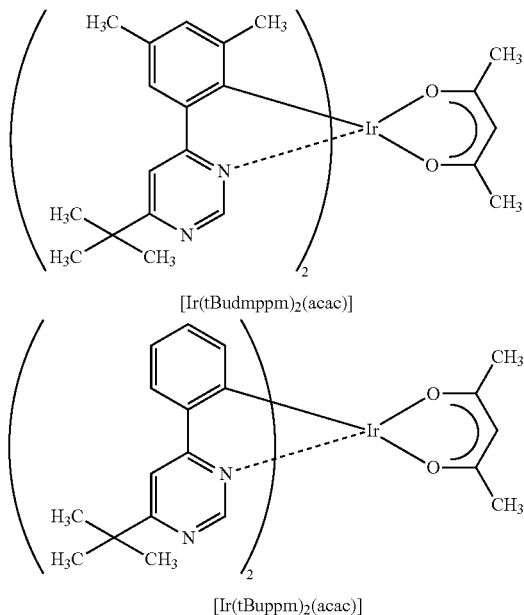

Figure 19:
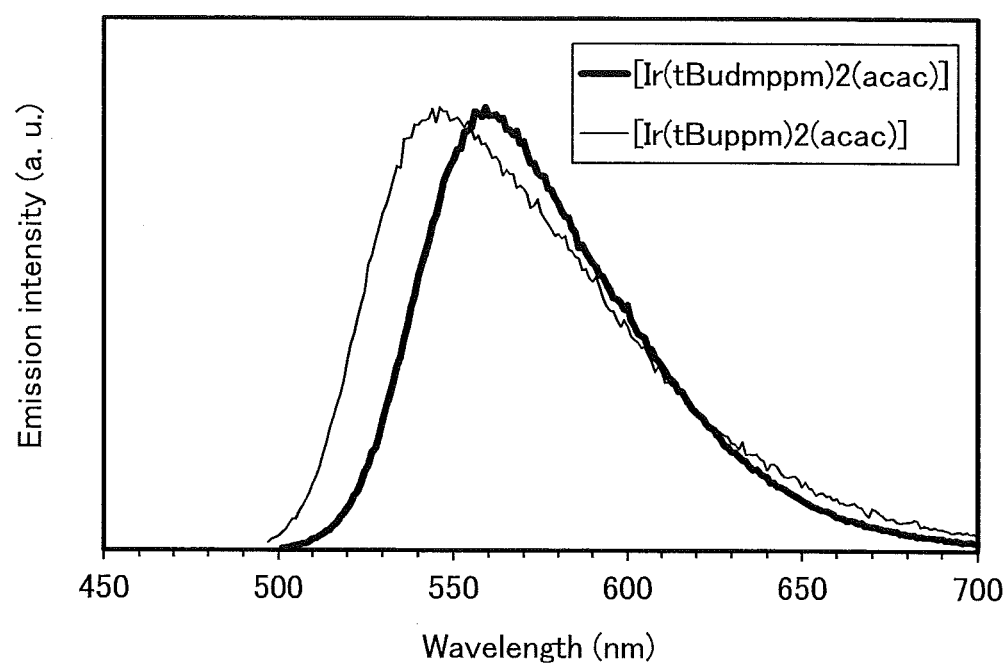
FIG. 19 shows results of comparison between emission spectra of organometallic iridium complexes.

The emission spectra were each measured using a degassed dichloromethane solution with a fluorescence spectrophotometer as in the above-described method. FIG. 19 shows the measurement results. The measurement results confirm that the emission wavelength of [Ir(tBudmppm)$_2$(acac)] that has the structure in which the phenyl group that is bonded to the pyrimidine skeleton and bonded to iridium has two substituents (methyl groups) at the 4-position and the 6-position is slightly longer than the emission wavelength of [Ir(tBuppm)$_2$(acac)] that has the structure in which the phenyl group that is bonded to the pyrimidine skeleton and bonded to iridium does not have such substituents.

Thus, the organometallic iridium complex of one embodiment of the present invention having the quinoxaline skeleton has the structure in which the phenyl group that is bonded to the quinoxaline skeleton and bonded to iridium has two substituents at the 4-position and the 6-position, so that the emission wavelength of the organometallic iridium complex can be located on the long-wavelength side. In addition, this enables a novel organometallic iridium complex that emits near-infrared light (emission wavelength: around 700 nm) to be provided.

EXPLANATION OF REFERENCE

101: first electrode, 102: EL layer, 103: second electrode, 111: hole-injection layer, 112: hole-transport layer, 113: light-emitting layer, 114: electron-transport layer, 115: electron-injection layer, 116: charge-generation layer, 201: anode, 202: cathode, 203: EL layer, 204: light-emitting layer, 205: phosphorescent compound, 206: first organic compound, 207: second organic compound, 301: first electrode, 302(1): first EL layer, 302(2): second EL layer, 302(n−1): (n−1)th EL layer, 302(n): n-th EL layer, 304: second electrode, 305: charge-generation layer (I), 305(1): first charge-generation layer (I), 305(2): second charge-generation layer (I), 305(n−2): (n−2)-th charge-generation layer (I), 305(n−1): (n−1)-th charge-generation layer (I), 401: element substrate, 402: pixel portion, 403: driver circuit portion (source line driver circuit), 404a, 404b: driver circuit portion (gate line driver circuit), 405: sealant, 406: sealing substrate, 407: wiring, 408: flexible printed circuit (FPC), 409: n-channel FET, 410: p-channel FET, 411: switching FET. 412: current control FET, 413: first electrode (anode), 414: insulator, 415: EL layer, 416: second electrode (cathode), 417: light-emitting element, 418: space, 1100: substrate, 1101: first electrode, 1102: EL layer, 1103: second electrode, 1111: hole-injection layer, 1112: hole-transport layer, 1113: light-emitting layer, 1114: electron-transport layer, 1115: electron-injection layer, 8001: lighting device, 8002: lighting device, 8003: lighting device, and 8004: lighting device.

This application is based on Japanese Patent Application serial no. 2013-125429 filed with the Japan Patent Office on Jun. 14, 2013, the entire contents of which are hereby incorporated by reference.

The invention claimed is:
1. A compound represented by Formula (G1):

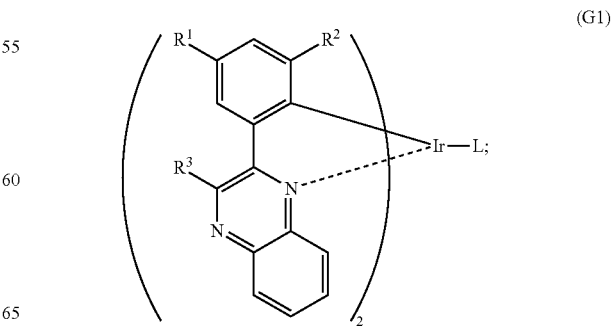

wherein:

L represents a monoanionic ligand, $R^1$ and $R^2$ separately represent a methyl group, an ethyl group, an isobutyl group, or a neopentyl group, $R^3$ represents a methyl group, an ethyl group, an isobutyl group, a 3,5-dimethylphenyl group, a 2-methylphenyl group, a 2,6-dimethylphenyl group, or a 3,5-diethylphenyl group, the monoanionic ligand is a ligand represented by Formula (L1)

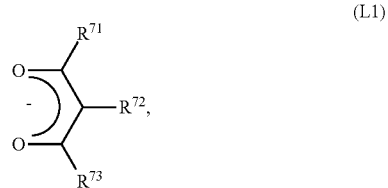

(L1)

and $R^{71}$ and $R^{73}$ represent a substituted or unsubstituted alkyl group having 3 to 6 carbon atoms, and $R^{72}$ represents hydrogen.

2. The compound according to claim 1, wherein the compound is represented by any of Formulae (100), and (118):

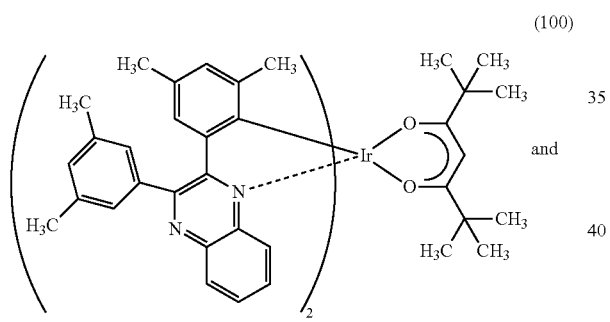

(100)

and

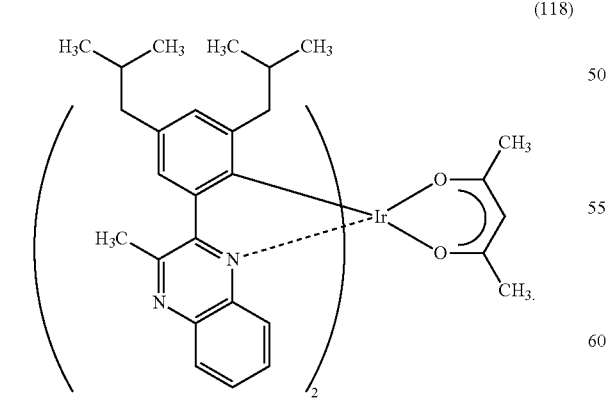

(118)

3. A light-emitting device comprising:

a layer between a pair of electrodes, the layer comprising a compound represented by Formula (G1):

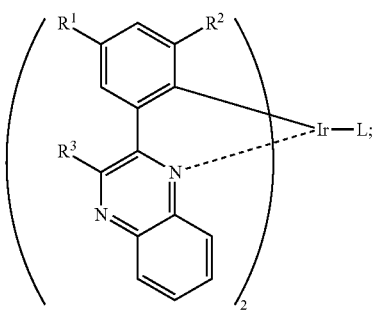

(G1)

wherein:

L represents a monoanionic ligand, $R^1$ and $R^2$ separately represent a methyl group, an ethyl group, an isobutyl group, or a neopentyl group, and $R^3$ represents a methyl group, an ethyl group, an isobutyl group, a 3,5-dimethylphenyl group, a 2-methylphenyl group, a 2,6-dimethylphenyl group, or a 3,5-diethylphenyl group.

4. The light-emitting device according to claim 3, wherein the monoanionic ligand is any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

5. The light-emitting device according to claim 4, wherein:

the monoanionic ligand is a ligand represented by any of Formulae (L1) to (L7):

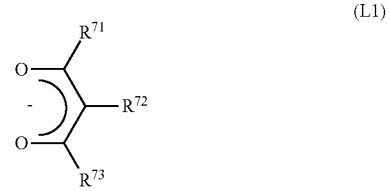

(L1)

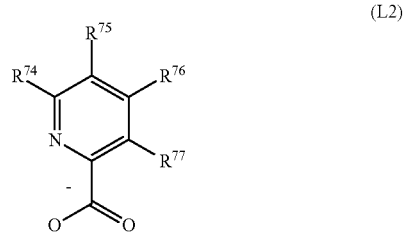

(L2)

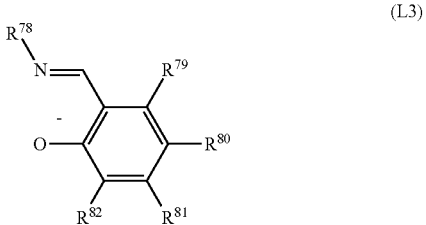

(L3)

-continued (L4)
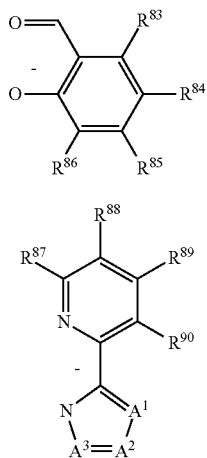

(L5)
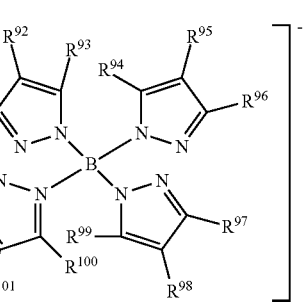

(L6)
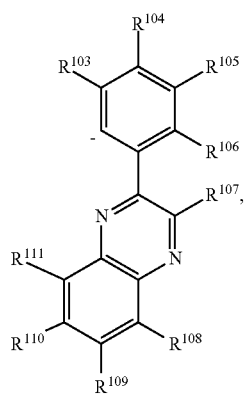

(L7)
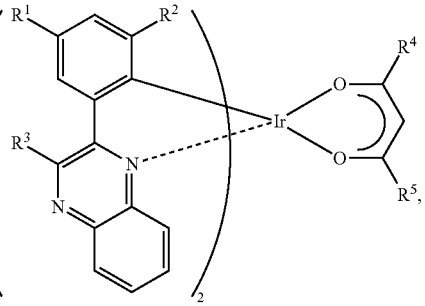

$R^{71}$ to $R^{111}$ separately represent hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms, $A^1$ to $A^3$ separately represent nitrogen, sp$^2$ hybridized carbon bonded to hydrogen, or sp$^2$ hybridized carbon having a substituent, and the substituent represents an alkyl group having 1 to 6 carbon atoms, a halogen group, a haloalkyl group having 1 to 6 carbon atoms, or a phenyl group.

6. The light-emitting device according to claim 3, wherein:

the compound is represented by Formula (G2):

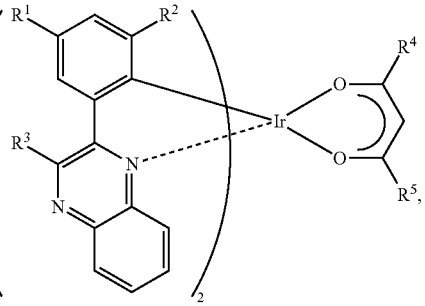

(G2)

and $R^4$ and $R^5$ separately represent hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms.

7. The light-emitting device according to claim 3, wherein the compound is represented by any of Formulae (100), (114), and (118):

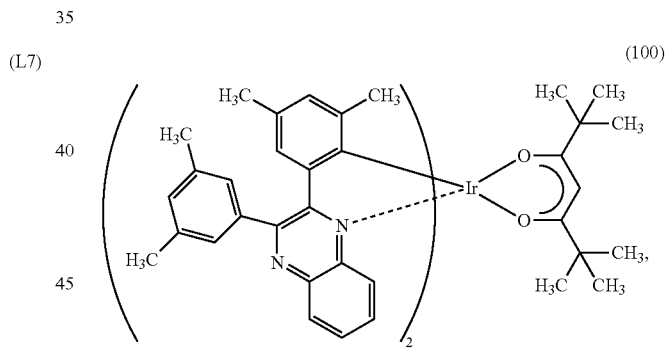

(100)

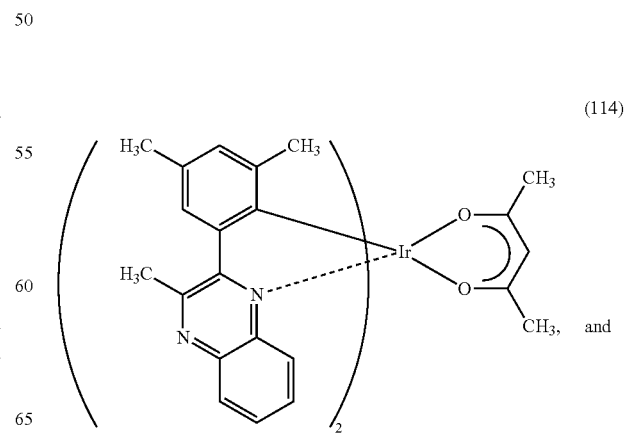

(114)

and

-continued
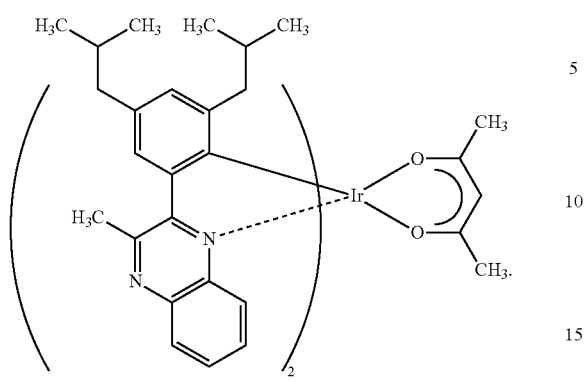
(118)
8. A lighting device comprising the light-emitting device according to claim 3.
* * * * *